United States Patent
Wolff et al.

(10) Patent No.: US 8,715,269 B2
(45) Date of Patent: *May 6, 2014

(54) DEVICES AND METHODS FOR INTRAORAL CONTROLLED DRUG RELEASE

(76) Inventors: Andy Wolff, Harutzim (IL); Ben Z Beiski, Kiryat-Ono (IL); Simon Herrlich, Villingen-Schwennigen (DE); Axel Schumacher, Dauchingen (DE); Sven Spieth, Dauchingen (DE); Stephan Messner, Villingen-Schwennigen (DE); Rachid Nouna, Villingen-Schwennigen (DE)

(*) Notice: Subject to any disclaimer, the term of this patent is extended or adjusted under 35 U.S.C. 154(b) by 115 days.

This patent is subject to a terminal disclaimer.

(21) Appl. No.: 13/406,514

(22) Filed: Feb. 27, 2012

(65) Prior Publication Data
US 2012/0220986 A1   Aug. 30, 2012

Related U.S. Application Data

(60) Provisional application No. 61/447,214, filed on Feb. 28, 2011.

(51) Int. Cl.
| *A61K 9/22* | (2006.01) |
| *A61M 37/00* | (2006.01) |
| *A61C 17/00* | (2006.01) |
| *A61C 17/02* | (2006.01) |
| *A61G 17/02* | (2006.01) |
| *A61C 5/00* | (2006.01) |

(52) U.S. Cl.
USPC ........... 604/892.1; 604/288.04; 604/93.01; 433/80; 433/215

(58) Field of Classification Search
USPC ........... 604/890.1–892.1, 288.01, 288.04, 604/93.01, 502; 433/80, 81, 215
See application file for complete search history.

(56) References Cited

U.S. PATENT DOCUMENTS

| 6,955,538 B1 * | 10/2005 | Borch et al. ............ 433/80 |
| 2007/0005043 A1 * | 1/2007 | Anderson ............ 604/890.1 |
| 2009/0210032 A1 * | 8/2009 | Beiski et al. ............ 607/59 |

* cited by examiner

*Primary Examiner* — Rebecca E Eisenberg

(57) ABSTRACT

Embodiments of the invention disclose a system for controlled oral drug delivery. The system comprising a removable device comprising a drug to be delivered, wherein the drug is delivered based on osmotic pressure generated in the removable device. Further, the system comprises a receptacle to hold the removable device in an oral cavity, and a base station configured to dock the removable device for determining information about one or more characteristics of the removable device.

17 Claims, 33 Drawing Sheets

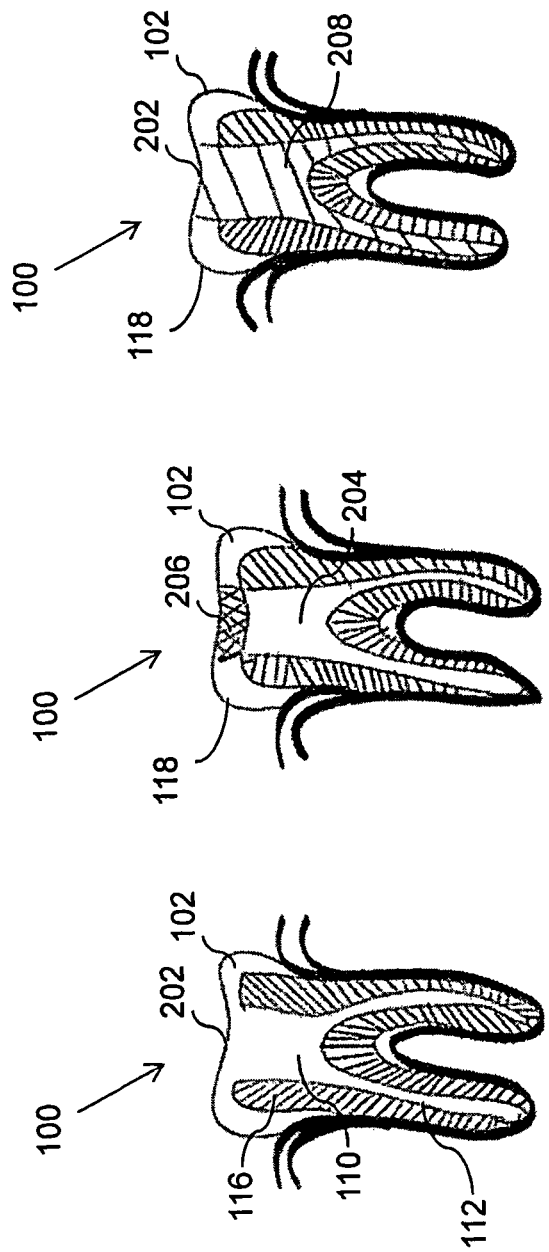

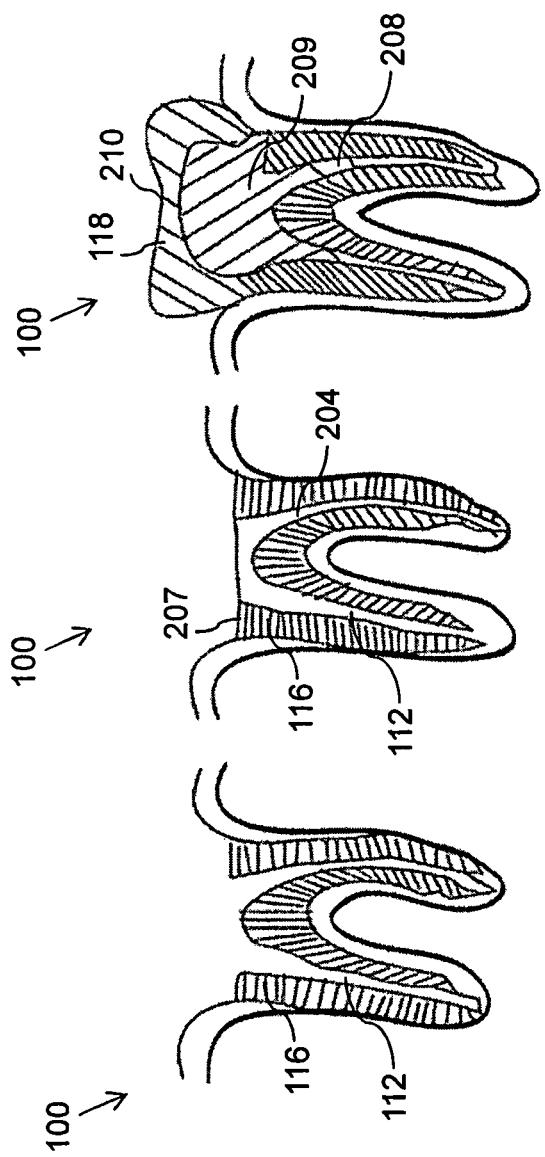

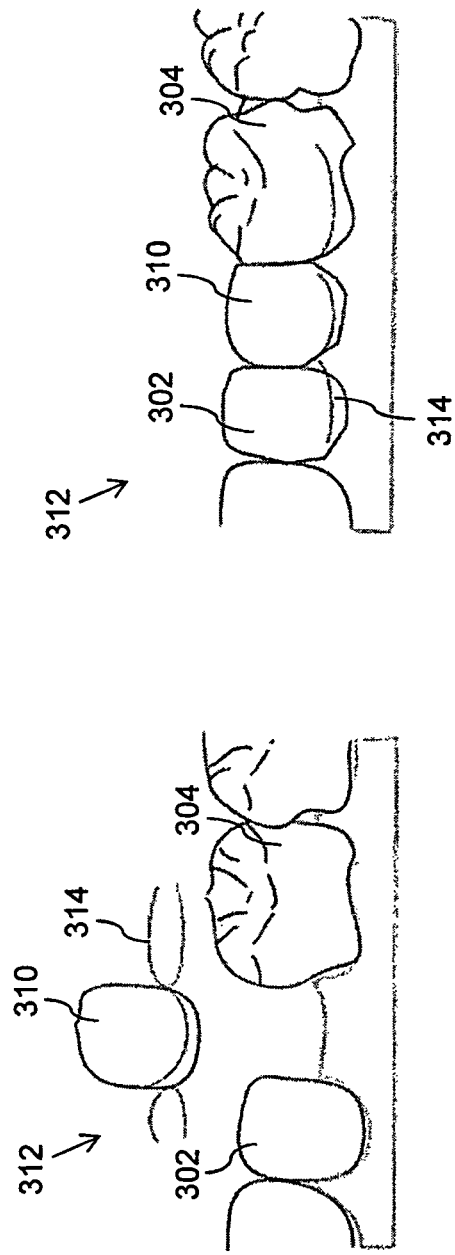

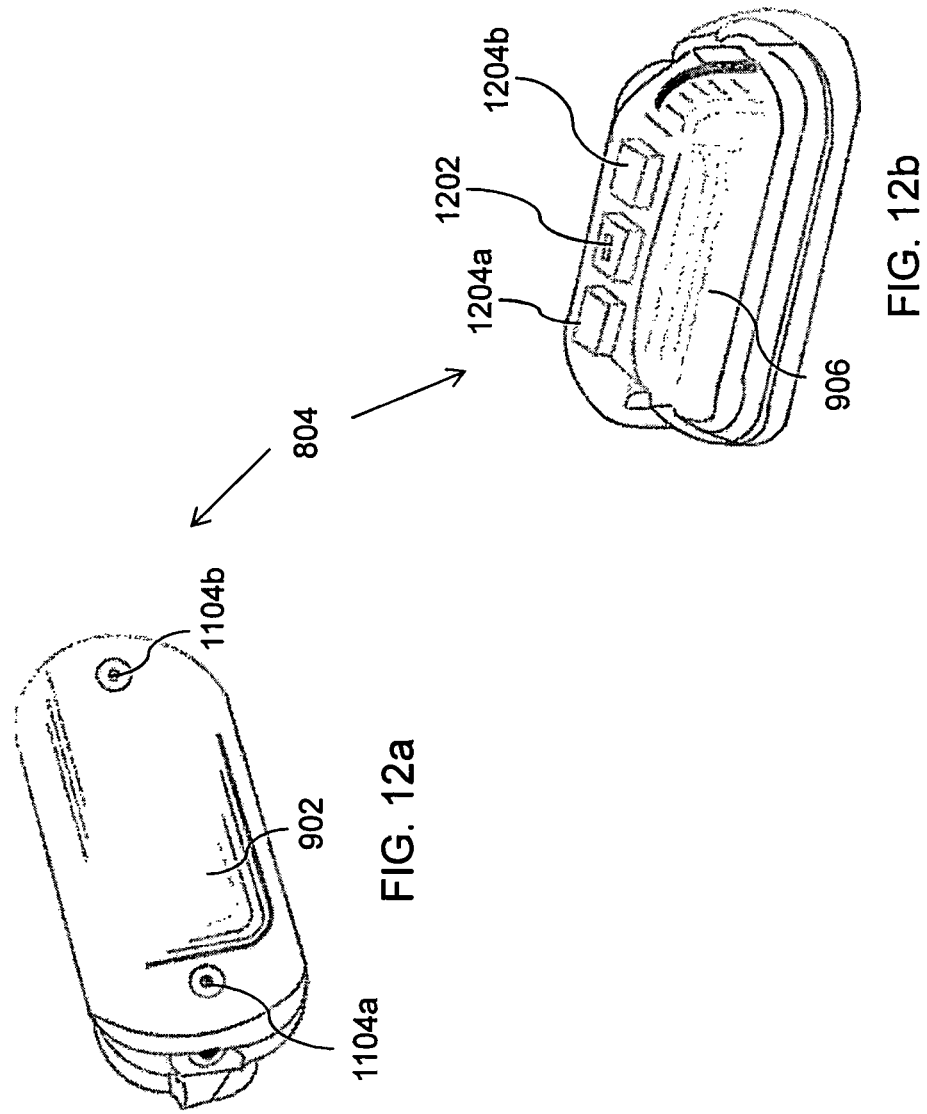

DEVICES AND METHODS FOR INTRAORAL CONTROLLED DRUG RELEASE

FIELD OF THE INVENTION

The present invention relates to medical devices, and more particularly, to oral devices and methods for controlled delivery of drugs.

BACKGROUND OF THE INVENTION

Oral drug administration is the most common drug delivery route. Typically, it is desirable that the drug is delivered at a controlled rate from the gastrointestinal tract to maintain a controlled level of the drug in the blood stream and the tissue. Further, controlled drug delivery is needed to control diurnal variations that may result from oral intake by a patient at specific times during the day. Yet, the degree to which the drug is available to the target tissue is affected by drug dissolution, drug degradation in the gastrointestinal tract, and drug absorption. This degree is referred to as bioavailability of orally administered drugs and is generally not constant with time. Some drugs have high bioavailability and may be dissolved and absorbed too fast, so as to peak shortly after intake. In these cases, controlled release dosage forms may be utilized that attempt to slow down the dissolution process. Some drugs have very low bioavailability and may be eliminated by the gastrointestinal tract before they are absorbed. In these cases, approaches that increase absorption and approaches that increase gastrointestinal retention may be employed.

The absorption of a drug (or of a drug precursor) into the systemic circulation is determined by the physicochemical properties, its formulations, and the route of administration of the drug. The route of administration may be oral, rectal, topical, by inhalation, or by intravenous administration. Oral administration includes swallowing, chewing, sucking, as well as buccal administration, i.e., placing a drug between the gums and cheek, and sublingual administration, i.e., placing a drug under the tongue. The advantage of chewing, sucking, as well as buccal and sublingual administration is that they lead to direct absorption via the oral cavity, where oral cavity additionally provide a route that avoids both the gastrointestinal tract and its losses, and the presystemic, first-pass metabolism, in the liver.

A prerequisite to absorption of the drug is the dissolution of drug. Typically, the extent of drug dissolution depends on whether the drug is in salt, crystal, or hydrate form. To improve the dissolution, disintegrants and other excipients, such as diluents, lubricants, surfactants (substances which increase the dissolution rate by increasing the wet-ability, solubility, and dispersibility of the drug), binders, or dispersants are often added during manufacture of the drugs.

Numerous gastrointestinal secretions, low pH values, and degrading enzymes may account to drug degradation in the gastrointestinal tract. Since luminal pH varies along the gastrointestinal tract, the drug must withstand different pH values. Further, interaction with blood, food stuff, mucus, and bile may also affect the drug. Reactions that may affect the drug, and reduce bioavailability are complex formations, for example, between tetracycline and polyvalent metal ions, hydrolysis by gastric acid or digestive enzymes, for example, penicillin and chloramphenicol palmitatehydrolysis. Further the complex formations may be conjugation in the gut wall, for example, sulfo-conjugation of isoproterenol or adsorption to other drugs, for example, digoxin and cholestyramine, and metabolism by luminal microflora.

Overall, low bioavailability is most common with oral dosage forms of poorly water-soluble and, slowly absorbed drugs. Insufficient time in the gastrointestinal tract is another common cause of low bioavailability. Ingested drug is exposed to the entire gastrointestinal tract for no more than 1 to 2 days and to the small intestine for only 2 to 4 hours. If the drug does not dissolve readily or cannot penetrate the epithelial membrane quickly, its bioavailability will be low. Moreover, age, sex, activity, genetic phenotype, stress, disease (e.g., achlorhydria, malabsorption syndromes), or previous GI surgery of the patient may also affect drug bioavailability.

Table 1 below [Encyclopedia of Controlled Drug Delivery, volume 2, edited by Edith Mathiowitz] summarizes some parameters of the oral route that affect drug bioavailability:

TABLE 1

| SECTION | AREA, $M^2$ | LIQUID SECRETION, LITER/DAY | PH VALUE | TRANSIT TIME, HOUR |
|---|---|---|---|---|
| Oral cavity | ~0.05 | 0.5-2 | 5.2-6.8 | Short |
| Stomach | 0.1-0.2 | 2-4 | 1.2-3.5 | 1-2 |
| Duodenum | ~0.04 | 1-2 | 4.6-6.0 | 1-2 |
| Small Intestine | 4500 (includingmicrovillies) | 0.2 | 4.7-6.5 | 1-10 |
| Large Intestine | 0.5-1 | ~0.2 | 7.5-8.0 | 4-20 |

In addition to the physical barrier of the epithelial cells, chemical and enzymatic barriers also affect drug absorption. Another important barrier to drug absorption is the presystemic, first-pass metabolism, primarily hepatic metabolism. The predominant enzymes in this metabolism are the multigene families of cytochrome P450, which have a central role in metabolizing drugs. It appears that variations in P450s between individuals lead to variations in their ability to metabolize the same drug.

Additionally, Multidrug Resistance (MDR) may be a barrier to drug absorption. MDR, which is a major cause of cancer treatment failure, is a phenomenon whereby cancer cells develop a broad resistance to a wide variety of chemotherapeutic drugs. MDR has been associated with over-expression of P-glycoprotein (P-gp) or Multidrug Resistance-associated Protein (MRP), which are transmembrane transporter molecules that act as pumps to remove toxic drugs from tumor cells. P-glycoprotein acts as a unidirectional efflux pump in the membrane of Acute Myelogenous Leukemia (AML) cells and lowers the intracellular concentration of cytotoxic agents, by pumping them out of leukemic cells. However, P-glycoprotein confers resistance to a variety of chemotherapy drugs, including daunorubicin.

Various approaches are available for increased drug absorption. Except for the route of intravenous administration, after dissolution, a drug must traverse several semi permeable biologic barriers before reaching the systemic circulation. A drug may cross the biologic barrier by passive diffusion, or by other naturally occurring transfer modes, for example, facilitated passive diffusion, active transport, or pinocytosis. Alternatively, a drug may be artificially assisted to cross the biologic barrier.

In passive diffusion, transport depends on the concentration gradient of the solute across the biologic barriers. Since the drug molecules are rapidly removed by the systemic circulation, drug concentration in the blood is low compared with that at the administration site, producing a large concentration gradient. The drug diffusion rate is directly proportional to that gradient. The drug diffusion rate also depends on other parameters, for example, the molecule's lipid solubility and size. Lipid-soluble drugs diffuse more rapidly through cell membranes than relatively lipid-insoluble drugs, because cell membranes are lipoid. Further, small drug molecules penetrate biologic barriers more rapidly than large ones.

Another naturally occurring transfer mode is facilitated passive diffusion, which occurs for certain molecules, such as glucose. It is believed that a carrier component combines reversibly with a substrate molecule at the cell membrane exterior. The carrier-substrate complex diffuses rapidly across the membrane, releasing the substrate at the interior surface. This process is characterized by selectivity and saturability: the carrier is operative only for substrates with a relatively specific molecular configuration, and the process is limited by the availability of carriers.

An alternative is nanotechnology, which derives its name from the size of the objects that it deals with. The size of these objects is usually smaller than 100 nanometers, and may even be at the molecular scale. As related to pharmaceuticals, the drugs particle are reduced to "nano" size, for smoother release, better dissolution pattern, better control on absorption, and decreasing the required dose.

Active transport, which is another naturally occurring transfer mode, appears to be limited to drugs that are structurally similar to endogenous substances. Active transport is characterized by selectivity and saturability and requires energy expenditure by the cell. It has been identified for various ions, vitamins, sugars, and amino acids.

Still another naturally occurring transfer mode is pinocytosis, in which fluids or particles are engulfed by a cell. The cell membrane encloses the fluid or particles, then fuses again, forming a vesicle that later detaches and moves to the cell interior. Like active transport, this mechanism requires energy expenditure. It is known to play a role in drug transport of protein drugs.

The foregoing discussion relates to naturally occurring transfer modes. Where these are insufficient, for example, in cases of macromolecules and polar compounds, which cannot effectively traverse the biological barrier, drug transport may be artificially induced.

Electro transport refers generally to electrically induced passage of a drug (or a drug precursor) through a biological barrier. Several electrotransport mechanisms are known. Iontophoresis involves the electrically induced transport of charged ions, by the application of low level, direct current (DC) to a solution of the medication. Since like electrical charges repel, the application of a positive current drives positively charged drug molecules away from the electrode and into the tissues; similarly, a negative current will drive negatively charge ions into the tissues. Iontophoresis is an effective and rapid method of delivering water-soluble, ionized medication. Where the drug molecule itself is not water-soluble, it may be coated by some water soluble entities. For example, the coating may be of Sodium Lauryl Sulfate (SLS), that may form, water soluble entities. Electroosmosis involves the movement of a solvent with the agent through a membrane under the influence of an electric field. Electrophoresis is based on migration of charged species in an electromagnetic field. Ions, molecules, and particles with charge carry current in solutions when an electromagnetic field is imposed. Movement of a charged species tends to be toward the electrode of opposite charge. The voltages for continuous electrophoresis is are rather high (several hundred volts). Electroporation is the process in which a biological barrier is subjected to a high voltage alternating-current (AC) surge, or pulse. The AC pulse creates temporary pores in the biological membrane, specifically between cells. The pores allow large molecules, such as proteins, Deoxyribonucleic Acid (DNA), Ribonucleic Acid (RNA), and plasmids to pass through the biological barrier. Iontophoresis, electroosmosis, and electrophoresis are diffusion processes, in which diffusion is enhanced by electrical or electromagnetic driving forces. In contrast, electroporation literally punctures the biological barriers, along cell boundaries, enabling a through passage of large molecules.

Generally a combination of more than one of the above-discussed processes is at work, together with passive diffusion and other naturally occurring transfer modes. Therefore, electrotransport refers to at least one, and possibly a combination of the aforementioned transport mechanisms, which supplement the naturally occurring transfer modes.

U.S. Pat. No. 5,298,017, to Theeuwes, et al., entitled "Layered electrotransport drug delivery system," describes an iontophoretic agent delivery device, having a layered structure and peripheral insulation, wherein ion transport occurs through two opposing surfaces of said device. The device is especially suited to agent delivery through body surfaces exposed to body fluids. U.S. Pat. No. 6,006,130, to Higo, et al., entitled "Iontophoresis electrode and iontophoresis device using the electrode", describes an iontophoresis electrode that is applicable to mucous membranes and oral mucous membranes, and especially capable of sticking directly on human oral mucous membranes and hence, administering medicine.

Other medical devices that include drug delivery by electrotransport are described, for example, in U.S. Pat. No. 5,674,196, to Donaldson, et al., U.S. Pat. No. 5,961,482, to Chien, et al., U.S. Pat. No. 5,983,131, to Weaver, et al., U.S. Pat. No. 5,983,134, to Ostrow, and U.S. Pat. No. 6,477,410, to Henley, et al., all of whose disclosures are incorporated herein by reference.

In addition to the aforementioned electrotransport processes, there are other electrically assisted drug delivery mechanisms, as follows:

Sonophoresis, or the application of ultrasound, induces growth and oscillations of air pockets, a phenomenon known as cavitation. This disorganizes lipid bilayers thereby enhancing transport. For effective drug transport, a low frequency of between 20 kHz and less than 1 MHz, rather than the therapeutic frequency, should be used. For example, U.S. Pat. No. 5,458,140, to Eppstein, et al., entitled "Enhancement of transdermal monitoring applications with ultrasound and chemical enhancers", describes a method of enhancing the permeability of the skin or mucosa to an analyte for diagnostic purpose utilizing ultrasound or ultrasound together with a chemical enhancer. The concentration of an analyte in the body is preferably determined by enhancing the permeability of the skin or other biological membrane optionally with a chemical enhancer, applying ultrasound optionally at a modulated frequency, amplitude, phase, or combinations thereof that further induces a local pressure gradient out of the body. Next, collecting the analyte, and utilizing the analyte collection data for calculating the concentration of the analyte in the body.

Other sonophoresis devices are described, for example, in U.S. Pat. Nos. 6,002,961 and 6,018,678 to Mitragotri, et al., U.S. Pat. Nos. 6,190,315 and 6,041,253 to Kost, et al., U.S. Pat. No. 5,947,921 to Johnson, et al. and U.S. Pat. Nos. 6,491,657, and 6,234,990 to Rowe, et al., all of whose disclosures are incorporated herein by reference.

Ablation, or the literal slicing of tissue, by various means, is another method of forcing drugs through a biological barrier. In addition to mechanical ablation, for example with hyperdemic needles, one may use laser ablation, cryogenic ablation, thermal ablation, microwave ablation, radio frequency ablation or electrical ablation. In essence, electrical ablation is similar to electroporation, but tends to be more severe.

U.S. Pat. No. 6,471,696, to Berube, et al., describes a microwave ablation catheter, which may be used as a drug delivery device. U.S. Pat. No. 6,443,945, to Marchitto, et al., describes a device for pharmaceutical delivery using laser ablation. U.S. Pat. No. 4,869,248, to Narula describes a catheter for performing localized thermal ablation, for purposes of drug administration. U.S. Pat. Nos. 6,148,232 and 5,983,135, to Avrahami, describe drug delivery systems by electrical ablation. The disclosures of all of these are incorporated herein by reference.

Various controlled release dosage forms are known. Oral controlled-release dosage forms are often designed to maintain therapeutic drug concentrations for at least 12 hours. Several controlled release mechanisms may be used, for example, as taught by Encyclopedia of Controlled Drug Delivery, volume 2, edited by Edith Mathiowitz, pp. 838-841. These are based on the use of specific substances, generally polymers, as a matrix or as a coating. These may be materials that degrade fast or slowly, depending on the desired effect. For example, when a drug's half-life in the body is too short, the drug may be coated with a slowly dissolving coating. Consequently, the drug must diffuse through the coating, which slows down (or increases) its half-life. Other coating materials form pores that fill with gastrointestinal fluids, increase the contact area between the drug and the gastrointestinal fluids, and reduce the diffusion path in the drug matrix, so as to increase the drug half-life. In these and other manners, modified forms of drug release prolong, delay or sustain the release of a drug in a passive, controlled manner, wherein passive refers to systems not controlled by electronics.

Modified drug release forms, for passive, controlled release include osmotic systems, membrane-coated tablets, enteric-coated dosage forms, multilayered tablets, pH independent controlled release tablets, a hydrogel plug dosage form, multiparticulate dosage forms, and the like. Osmotic systems rely on the uptake of water by the dosage form to increase the osmotic pressure within the system. The build-up of osmotic pressure drives the drug through an orifice in the dosage form to release the drug in a controlled manner. Membrane-coated tablets consist of water-soluble drug particles compressed to form a tablet core. A coating of a substantially insoluble polymer, for example, polyvinyl chloride, is applied to the tablet core, wherein the coating is mixed with a water soluble, pore-forming compound. Additionally, the solubility of the pore-forming compound may be pH dependent, to target a specific zone in the gastrointestinal tract. The rate of drug release is dependent on the pH level and on the extent of porosity in the coating, after the pores are formed. Enteric-coated dosage forms are dosage forms in which a drug core is coated with a polymeric mixture, formed of soluble and insoluble particles. The soluble particles dissolve in the intestinal fluids, exposing the insoluble particles. As a result, a micro porous layer is formed around the drug core and the drug slowly permeates through the pores.

Multilayered tablets consist of a drug core layered with several coatings, which may be of different solubilities, to provide release of drug at specific time intervals and (or) pH levels. As each layer dissolves, a pulsatile-type release is achieved. By modifying the types and amount of polymers used in the several coatings, the release rate may be adjusted. pH independent controlled release tablets are produced by wet granulating an acidic or basic drug blend with a buffering agent and appropriate excipients. The granules are then coated with, a film, which is permeable to gastrointestinal fluid, and the coated composite is compressed into a tablet. Upon oral administration, gastrointestinal fluid permeates the film coating. When in contact with the gastrointestinal fluid, the buffering agents adjust the pH value of the tablet; the drug dissolves and permeates out at a constant rate, independent of the pH level in the gastrointestinal tract. Hydrogel plug dosage form consists of a capsule having a water insoluble body sealed with a water-soluble cap, which further contains a hydrogel plug. When the capsule is swallowed, the water-soluble cap dissolves and exposes the hydrogel plug, which begins to swell. At a predetermined time after ingestion, the hydrogel plug is ejected and the drug is released into the gastrointestinal tract. Multiparticulate dosage forms generally consist of sugar or nonpareil pellets, which are spray coated with a drug, dried, and then spray coated with a second coating composition, which provides controlled release. The second coating composition is typically formed of polymers, which are partially soluble or insoluble in the gastric fluid, wherein the degree of solubility depends on the desired drug release pattern. The doubly coated pellets are placed in a capsule, for swallowing. A capsule may contain pellets of different types and release profiles.

Many of the orally administered drugs are absorbed efficiently in the upper gastrointestinal, tract, the stomach, and the proximal section of the small intestine but barely in the colon [See, Singh at al. J Controlled Release 63 (3), 235 (2000), and U.S. Pat. No. 5,443,843, to Curatolo et al.]. Yet, because the passage of the drug in the upper gastrointestinal tract, the stomach, and the proximal section of the small intestine is relatively fast, generally about 12 hours, the drug bioavailability becomes limited. This implies that a dosage form is operative primarily during that time span. Hence, prolonging the retention time of the drug in the upper sections is of utmost importance for increased bioavailability. [See, Hwang et al. Crit. Rev. Ther. Drug Carrier Syst, 15(3), 243 (1998)].

An answer to the above discussed need may be a long-term gastric retention device, which is taken orally and which is adapted for long-term drug release in the upper gastrointestinal tract. A long-term gastric retention device may be especially useful in cases of drugs taken over long periods, as in instances of chronic diseases and hormonal treatments. It will also simplify treatments that combine different drugs.

The medication that may be considered for long-term gastric retention devices must fit the following criteria: (a) large therapeutic range, so that deviations from the amount of released drug, above or below the predicted level, will not cause significant symptoms; and (b) overdoses will not endanger the patient. Potential drug candidates include: Analgesics, Anxiolytics, Antimigroine drugs, Sedatives, Antipsihotics, Anticonvulsants, Antiparcinsons, Antiallergic drugs, Antidepressants, Antiemetics, Astma-profilactics, Gastric-hypoacidics, Anticonstipation drugs, Intestinal antiinflammatory agents, Antihelmintics, Antianginals, Diuretics, Hypolipidemic agents, Anti-inflammatory drugs, Hormones, Vitamins, and Antibiotics.

Several approaches for long-term gastric-retention device are available:

(A) An anintragastric floating system: this system is designed to float in the gastric fluid. Three major techniques that have been used to generate buoyancy in the gastric fluid are as (follows: (i) A mixture of bicarbonate and gastric fluid generates carbon dioxide, which remains trapped within a matrix of the dosage form. This causes the dosage form to float in the stomach, so as to prolong its residence in the stomach. Similarly, another gas may be produced; (ii) A low-density core system is formed of buoyant materials, such as air, $CO_2$ or gels. It is coated by an outer layer of a dosage form, adapted for controlled release; and (iii) A gel forming hydrophilic polymer, which upon contacting with the gastric fluid forms a gelatinous shell. It may be used to produce a hydrodynamic-balanced system, whose buoyancy is ensured by its dry or hydrophobic core. The gelatinous shell is also responsible for the controlled release of the drug. However, the aforementioned floating devices have a stomach residence time of only a few hours, and their action is dependent upon the amount of food and water in the stomach. Therefore, performance of these devices is non-uniform and difficult to predict.

(B) High-density system is based on sinking the device to the bottom of the stomach. Thus, the device is usually made of heavy materials. Initially, this approach looked promising, but studies have since shown that there is no appreciable gastric retention.

(C) A mucoadhesive system: this adhesive system is able to adhere to the mucous walls of the stomach, and is expected to remain in the stomach, for the duration of the mucous layer turnover. However, it also binds to almost any other material it comes in contact with, for example, gelatin capsules, proteins, and free mucous, in the gastric fluid. Another obstacle is that its adhesiveness is pH-dependent, and higher than normal gastric pH levels reduce the adhesiveness dramatically. Therefore, experimental results were disappointing, and no substantial increase in residence time in the stomach was observed.

(D) A magnetic system: an extracorporeal magnet is placed over the stomach, and small magnetized particles, within the dosage form. Thus, preventing the dosage form from leaving the stomach. Even though some success has been reported, the viability of these systems is in doubt. The doubt arises because the extracorporeal magnet has to be carried and placed very accurately, in order to obtain the desired results. New, more convenient ways to apply a magnetic field have to be found to improve this concept.

(E) An expansible system is based on a sharp dimensional change, in the stomach. Several methods have been proposed for this system: (i) a hydrogel that swells upon contact with the gastric fluid; (ii) an osmotic device that contains salt or sugar, and is surrounded by a semi-permeable membrane; and (iii) a system containing liquid with low boiling point, that turns into gas at body temperature and inflates the device to its desired size, wherein simultaneous with the swelling, a controlled release begins. However, these systems suffer from a slow swelling rate and therefore are not retained in the stomach. Furthermore, the ability to swell to a desired size and the degradation process that follows, still pose substantial challenges.

(F) A superporous, biodegradable, hydrogel system that is based on the swelling of a unique hydrogel system, which is superporous in nature. The system is synthesized by crosslinking polymerization of various vinyl monomers in the presence of gas bubbles formed by chemical reaction of acid and $NaHCO_2$. Compared to other expansible systems, it has a much higher swelling level and swells at a much faster rate than conventional hydrogels, and relatively attaining a desired expanded form in minutes, as opposed to hours. However, the system is mechanically weak, so it breaks down, leading to short residence times in the stomach.

(G) A mechanical, expansible system: this system is based on a mechanical device, which unfolds or extends from an initial, compact size, to an extended form that prevents passage through the gastric pylorus. At present, the mechanically expansible system is the most promising, in the gastric retention field. However, various technical problems, related to its performance are yet to be solved.

Therefore, at present, reliable and efficient long-term gastric retention devices are not available.

Typically, effectiveness of treatment of any medication depends on a patient's adherence to prescription schedule. Low adherence with prescribed treatments is ubiquitous, yet it may undermine the success of a treatment. Typical adherence rates are about 50% for medications and are much lower for lifestyle prescriptions and other more behaviorally demanding regimens [See, Haynes R B, McDonald H P, Garg A X. JAMA 288(22):2880-3 (2002)]. In fact, a Hungarian study reported that one third of hypertension patients took the medication irregularly, despite of the potentially life-threatening implications [See, Rapi J. Ory Hetil 143(34):1979-83 (2002)] Another survey showed that 62.4% patients with familial hypercholesterolemia were not taking their prescribed cholesterol-lowering medication [See, Umans-Eckenhausen M A, Defesche J C, van Dam M J, Kastelein J J. Arch Intern Med 163(1):65-8 (2003).] In fact, missed doses occur more frequently than taking an overdose. [See, De Klerk E, Van Der Heijde D, Landewe R, Van Der Tempel H, Urquhart J, Van Der Linden S. J Rheumatol 30(1):44-54 (2003).]

Conventional methods of improving medication adherence for chronic health problems are complex, labor-intensive, and not very effective. Improving adherence to long-term regimens requires a combination of information about the regimen, counseling about the importance of adherence, advice on how to organize medication regimen in your life, reminders, rewards and recognition for the patient's efforts to follow the regimen, and social support from family and friends. The full benefit of medication is not realized at low levels of adherence. Therefore, more studies and innovative approaches to assist patients to follow prescriptions are needed [See, McDonald H P, Garg A X, Haynes R B. JAMA 288(22):2868-79 (2002)].

Another issue in drug prescription is the efficacy and safety of both new and existing drugs. Efficacy and safety are related factors in a drug's clinical profile. Drug doses are calculated according to a therapeutic window for each drug, which is the range of drug concentration in the blood, ranging between the minimum effective therapeutic concentration and the minimum toxic concentration. The width of the therapeutic window may be measured by a therapeutic index that is the ratio between the median lethal dose and the median effective dose. This is a safety margin for using a specific drug. The wider the index, the safer the drug.

The accepted rule in pharmaceutics is that a drug that has less than a twofold difference between its toxic and effective doses is considered to have a "narrow therapeutic index," and its use must be carefully monitored. Yet, several clinically important drugs have narrow therapeutic indices. These include anti-AIDS agents like AZT, antibiotics like ciprofloxacin, CNS agents like Levodopa, and anti diabetic agents. Various techniques are available for providing scheduled medication to the patient, for example, chronotheraphy, Dental structure and dental implements, Root Canal, bridge, root canal, dental implants, crown and the like.

Chronotherapy: According to Stehlin [See, Stehlin I., "A Time to Heal: Chronotherapy Tunes In to Body's Rhythms," US Food and Drug Administration], our body's physiological clock takes its cue from the solar system, affecting blood pressure, blood coagulation, blood flow, and other functions. Several types of physiological cycles may be defined, as follows: (i) ultradian: cycles that are shorter than a day (for example, sleep cycles of about 90 minutes); (ii) circadian: daily cycles (such as sleeping and waking patterns); (iii) infradian: cycles that are longer than 24 hours (for example, monthly menstruation); and (iv) seasonal: for example, a Seasonal Affective Disorder (SAD) that causes depression in susceptible people during the short days of winter.

For instance, the normal lung function under goes circadian changes and reaches a low point in the early morning hours. This dip is particularly pronounced in people with asthma. Therefore, chronotherapy may be especially useful for asthma. It is aimed at getting maximal effect from bronchodilator medications during the early morning hours. For example, the bronchodilator, uniphyl, a long-acting theophylline preparation, manufactured by Purdue Frederick Co. of Norwalk, Corm., and approved by FDA in 1989 may be used for chronotherapy. Taken once a day in the evening, uniphyl causes theophylline blood levels to reach their peak and improve lung function during the early morning hours.

Additionally, according to Stehlin, chronotherapy may be useful in the treatment of cancer, arthritis, hypertension, diabetes, heart-attacks, sexual dysfunction, and eating and sleeping disorders. For example, animal studies suggest that chemotherapy may be more effective and less toxic if cancer drugs are administered at carefully selected times. It appears that there may be different chronobiological cycles for normal cells and tumor cells. Thus, if administration of cancer drugs is timed with the chronobiological cycles of tumor cells, it will be more effective against the cancer and less toxic to normal tissues.

Furthermore, chronobiological patterns have been observed with arthritis pain. People suffering from osteoarthritis, the most common form of the disease, tend to be in pain at night. But for people with rheumatoid arthritis, the pain usually peaks in the morning. When using chronotherapy for arthritis, both nonsteroidal anti-inflammatory drugs and corticosteroids may be timed to ensure that the highest blood levels of the drug coincide with the times of peak pain.

Techniques exist that attach devices either in the mouth or in other parts of the body to control drug release. For example, the device may be attached to or placed around teeth or implanted into the gum.

Dental structure and dental implements: the following is a brief overview of a tooth structure and of known techniques for dental repair and reconstruction. With reference to FIG. 1, a typical cross-sectional view of a tooth 100 is shown. As seen in the FIG, the basic parts of a tooth are: a crown 102, the portion of tooth above a gum 104, and a root or roots 106, which anchor the tooth in a jawbone. A pulp 108 is arranged within a pulp chamber 110 and within a root canal or root canals 112.

Crown 102 is formed of an inner structure of dentine 116 and an external layer of enamel 114, which defines a chewing surface 118. There may be one, two, or more roots 106. Each root has an external layer of cement 120, inner structure of dentine 116, and one root canal 112. Pulp 108 is formed of tiny blood vessels, which carry nutrients to the tooth, and nerves, which give feeling (senses) to the tooth. The blood vessels and the nerves enter root canals 112 via accessory canals 122 and root-end openings 124.

Tooth 100 may define a cylindrical coordinate system of a longitudinal axis 'x', and a radius 'r'. A coronal or incisal end 126 may be defined as the end above gum 104 and an apical end 128 may be defined as the end below the gum.

Various intra oral devices and dental reconstruction and repair methods are discussed in conjunction with FIGS. 2A to 7C, here in below.

A root canal treatment may be required when the pulp is diseased or injured and dies. Common causes of pulp death are a deep cavity, a cracked filling, or a cracked tooth. Bacteria then invade the tooth and infect the pulp. The inflammation and infection may spread down the root canal, often causing sensitivity to hot or cold foods and resulting into pain. Root canal treatment involves removing the diseased pulp. After this, cleaning and sealing the pulp chamber and root canals. Lastly, filling or restoring the crown. The steps in root canal therapy are illustrated in FIGS. 2A to 2G.

FIGS. 2A, 2B, and 2C illustrate a root canal treatment in which crown 102 was not severely damaged. As seen in FIG. 2A, an opening 202 is made, generally through crown 102 and dentine 116, into the pulp chamber 110. Pulp 108 (FIG. 1) is then, removed with a tiny file (not shown). Further, pulp chamber 110 and root canals 112 are cleaned and shaped to a form that may be filled.

As seen in FIG. 2B, medications 204 may be applied to pulp chamber 110, and root canals 112, for a period of about two weeks, to disinfect them. A temporary filling 206 may be placed in crown opening 202 to protect the tooth between dental visits.

As seen in FIG. 2C, after removing medications 204 and temporary filling 206 of FIG. 2B, pulp chamber 110 and root canals 112 are cleaned and filled with a permanent filling 208, and chewing surface 118 is restored.

FIGS. 2D-2G illustrate situations in which crown 102 (FIG. 1) was severely damaged. As seen in FIG. 2D, remnants of crown 102 are removed, and root canals 112 are cleaned and shaped as discussed above.

As seen in FIG. 2E, medications 204 may be applied to root canals 112, for a period of about two weeks, to disinfect the root canals. A sealing layer 207 may then be applied over the exposed dentine, to protect it until the next dental visit.

As seen in FIG. 2F, after removing medications 204 of FIG. 2E, root canals 112 are cleaned and filled with permanent filling 208. A core 209 of permanent filling 208 is then constructed over the roots, to restore the crown, and a mold (not shown) is taken of the remaining tooth structure and core 209. A temporary structure 210 is then placed over the remaining tooth structure and core 209.

As seen in FIG. 2G, a permanent, enamel-like structure 212 is prepared from the mold, and placed over core 209.

On the other hand, when teeth are lost, replacement options include bridges implant and dentures. A bridge may be used to fill a gap of up to four teeth, where there are healthy natural teeth on either side of the gap. FIGS. 3A-3F illustrate an application of a three-unit bridge 300 between two healthy teeth 302 and 304. As seen in FIGS. 3A-3B, the dentist will prepare teeth 302 and 304 on either side of the gap by removing portions of the enamel and dentin, leaving stumps 306 and 308. Impressions or molds of stumps 306 and 308 and the gap between them are taken for the construction of the bridge. In the meantime, a temporary bridge is applied to protect the exposed stumps and provisionally restore the missing teeth.

As seen in FIGS. 3C and 3D, the dentist then fits bridge 300, where the bridge 300 includes a prosthetic tooth crown 310, over stumps 306 and 308. If the fit is good, the dentist cements bridge 300 into place, restoring function to the area.

FIGS. 3E-3F illustrate an alternative technique: a bridge 312 may be formed including a prosthetic tooth crown 210 and anchors 314, such that the anchors 314 are adapted to clamp onto healthy teeth 302 and 304. Unlike bridge 300 of FIGS. 3C-3D, which is cemented into place, bridge 312 may be removed, for example, for cleaning.

As an alternative to a bridge, a dental-implant-and-prosthetic-tooth-crown 400 may be used. As seen in FIGS. 4A-4C, dental-implant-and-prosthetic-tooth-crown 400 includes, for example, a dental implant or fixture 402, surgically implanted into the bone that grows around the tooth 400. Once dental implant 402 is anchored into the bone, a stump 404 is mounted on it and prepared to accept prosthetic tooth crown 310.

In a situation where several teeth are missing, dentures 500 may be used, containing a plurality of prosthetic tooth crowns 310, as seen in FIGS. 5A-5C. It is possible to get either full dentures, of all the teeth, as seen in FIG. 5A, or partial dentures, of fewer teeth, as seen in FIG. 5B. Full dentures are form-fitted to the gum ridges, creating an adhesive effect that keeps them in place. Partial dentures may be adapted to fit around the natural teeth, to help them stay in place. Additionally, as seen in FIG. 5C, a dental implant post 402 may be used to further secure the dentures.

In some cases, the root of the tooth is intact, but its upper portion is severely decayed or broken. An artificial crown may then be placed on the tooth, as seen in FIGS. 6A-6C. FIG. 6A illustrates a broken tooth 602. As seen in FIG. 6B, it is prepared by removing a portion of the enamel and dentin, and exposing a stump 604, As seen in FIG. 6C, a crown 606 is then cemented over stump 604, hence, restoring the chewing surface.

Braces are other known orthodontics dental devices. FIG. 7A illustrates braces 700 that include molar bands 702, arch wires 704, and brackets 706. FIG. 7B illustrates braces 710, which includes a metal or plastic plate 712, and wires 714 and 716. The metal plate 12 is adapted to fit against the roof of the mouth. FIG. 7C illustrates invisible braces 720. In general, the braces of FIGS. 7A-7C may be easily removed, for example, for cleaning.

Various slow-releasing devices to be attached to or placed around teeth or implanted into the gum are available, for example U.S. Pat. No. 3,624,909, U.S. Pat. No. 3,688,406, U.S. Pat. No. 4,020,558, U.S. Pat. No. 4,175,326,U.S. Pat. No. 4,681,544, U.S. Pat. No. 4,685,883, U.S. Pat. No. 4,837,030, U.S. Pat. No. 4,919,939, U.S. Pat. No. 6,264,974, and U.S. Pat. No. 6,399,610. The devices mentioned above and those quoted here in after deliver a medication into the oral cavity, but these devices lack a controlled rate of drug delivery for extended time periods which is of utmost importance in the prevention and treatment of the heretofore mentioned diseases and conditions.

U.S. Pat. No. 4,020,558, to Cournut, et al., entitled "Buccal implant for administering solubilizable products," describes a buccal implant constituting at least one plate of small thickness formed of a material containing solubilizable substances. The plate is fastened to the teeth and maintained in close proximity to the gum in order to pass the solubilizable substances into the saliva.

U.S. Pat. No. 4,837,030, to Valorose, Jr., et al., entitled "Novel controlled release formulations of tetracycline compounds," describes pharmaceutical compositions comprising spherical granules including thereon or therein a 7- or 9-alkylamino-6-deoxy-6-demethyltetracycline or an acid-addition salt thereof blended with at least one excipient adapted to control the rate of drug release in the stomach and in the intestine in order not to produce nausea or dizziness upon oral administration during antibacterial therapy. The invention discloses an orally administrable pharmaceutical composition comprising beads coated with an ultra-thin layer of a polymer that erodes under gastric conditions. When suspended in water, more than 90% of the pharmaceutical agent is released from the composition in between 20 to 90 minutes.

U.S. Pat. No. 4,919,939, to Baker, entitled "Periodontal disease treatment system," describes a controlled release drug delivery system for placement in the periodontal pocket, gingival sulcus, tooth socket, wound or other cavity within the mouth. The system incorporates drug-containing micro-particles in a fluid carrier medium, and is effective in the environment of use for up to 30 days. The patent discloses a controlled release drug delivery system comprising a polymeric matrix, which dissolves, releasing the drug contained therein within 10 to 18 hours, upon the action of the saliva.

U.S. Pat. No. 6,143,948, to Leitao, et al., entitled "Device for incorporation and release of biologically active agents," describes an implantable device coated with a layer of calcium phosphate and optionally one or more biologically active substances such as growth factors, lipids, (lipo) polysaccharides, hormones, proteins, antibiotics or cytostatics. The implant may be used for biomedical use, i.e. as a bone substitute, a joint prosthesis, a dental implant (prosthodontics), a maxillofacial implant, and the like.

U.S. Pat. No. 6,264,974, to Madhat, entitled "Buccal and sublingual administration of physostigmine", describes Physostigmine administered buccally or sublingually in non-sustained release dosage form, providing prolonged blood levels. This active agent is physically compounded with materials of some or all of classes of ingredients that function as pH controls, preservative agents, viscosity control agents, absorption enhancers, stabilizing agents, solvents, and carrier vehicles. This compounding will produce a pharmaceutical composition in the form of a liquid, tablet, gel, patch or lozenge for administration of the active agent, Physostigmine, by absorption through the buccal or sublingual mucosa of the patient.

U.S. Pat. No. 6,399,610, to Kurkela, et al., entitled "Transmucosal formulations of levosimendan," describes a method of administering transmucosally, particularly to oral or nasal mucosa, levosimendan or a pharmaceutically acceptable salt thereof to a patient. The method comprises contacting an intact mucous membrane with a source of levosimendan, and maintaining said source with said mucous membrane for a sufficient time period to deliver levosimendan to the patient.

Other patent disclose implanted devices, either in the mouth or in other parts of the body, including diverse mechanisms to control drug release. U.S. Pat. No. 4,252,525 to Child, entitled "Dental implant," describes a tooth prosthesis located in a mandible tooth socket having a root supporting a crown. An elastic body of ethylene vinyl acetate (EVA) copolymer surrounds and is bonded to the stem. The fabric has a pyrolite carbon outer skin. The upper edge of the fabric is spaced from the crown and head whereby the elastic body allows limited movement of the crown relative to the fabric. Ionic silver is released from the bands, which provides antibacterial action. In one form, a silver wire contained in the root and connected to a band and a source of direct current releases ionic silver into the surrounding tissue. In another form, the root, crown, and body have passages for accommodating drug materials and silver compounds.

U.S. Pat. No. 4,871,351, to Feingold, entitled "Implantable medication infusion system," describes an implantable medication delivery system comprising an implantable unit with a refillable reservoir, a catheter connected thereto, and a pumping mechanism activated by a microcomputer or microprocessor for pumping medication from the reservoir through the catheter into the body. The implantable medication unit receives information and control commands via a telemetry link from an external controller unit having a microprocessor.

The external controller receives feedback in the form of intermittent sampling of blood using enzyme strips and a reflectance meter and/or additional sensor(s) which measure(s) physiological parameter(s) such as heart rate or blood pressure or temperature or skin resistivity. The feedback information is processed by the external unit in accordance with a mathematical model of the patient and the relevant parameters are transmitted to the implanted unit which adjusts its delivery profile according to a prescribed algorithm. The external unit may also detect an alarm condition and take appropriate steps, e.g. abort infusion.

U.S. Pat. No. 5,090,903, to Taylor, et al., entitled "Dental prosthesis with controlled fluid dispensing means," describes a system for automatically and progressively dispensing fluids into an individual's mouth comprising a dental prostheses such as a bridge having an interior cavity with a plurality of chambers defined therein. A first passageway communicates between the inner chamber and the interior of the mouth for progressive delivery of fluid from the chamber into the mouth. A second passageway communicates between the outer chamber and the outer surface of the bridge and functions as a vent. The walls, openings, and passageways are positioned and oriented such that fluid is dispensed into the mouth progressively from the inner chamber during waking hours when the wearer is in a standing or upright position and is not dispensed during the night time or sleeping hours when the wearer is in an inclined or lying position. The wall holes are positioned such that the inner chamber of the cavity is refilled during sleeping hours for subsequent dispensing when the wearer wakes and arises.

U.S. Pat. No. 5,196,002, to Hanover, et al., entitled "Implantable drug delivery system with piston actuation," describes an implantable drug delivery system including a housing having a base end and a discharge end, for holding drug solution at the discharge end, a valve disposed at the discharge end to allow a drug solution to flow from inside the housing, through the valve and out of the housing when solution pressure is applied to the valve, a piston slidably disposed in the housing to slide between the base end and discharge end to force solution toward the discharge end and out the valve, and a spring disposed in the housing between the piston and the base end thereof for urging the piston toward the discharge end. A timing circuit is disposed to supply release signals sequentially, and as a result the piston is allowed to move toward the discharge end of the housing to thereby discharge or bolus of drug solution from the housing, until the next shortest unreleased tether stops further movement of the piston.

U.S. Pat. No. 5,433,952, to Sipos, entitled "Intraoral medicament-releasing device," describes controlled rate-release devices for releasing a pharmaceutically active agent into the oral cavity by the dissolving action of the saliva. U.S. Pat. No. 5,558,640, to Pfeiler, et al., entitled "System for infusion of medicine into the body of a patient," describes a system for infusing medicine into the body of a patient including an implantable infusion apparatus containing a dosing unit with a reservoir for the medicine and a medicine delivery pump for pumping doses of the medicine from the reservoir into the patient. The infusion apparatus also includes a sensor for sensing a parameter of the patient for controlling the dosing of medicine according to the sensed parameter. The dosing unit and the sensor are galvanically separable and are each provided with separate telemetry communication units for communication with an external programmer/controller. The external programmer/controller includes telemetry communication units for selectable communication with the dosing unit or the sensor or both simultaneously. The telemetry communication units of the external programmer/controller, the dosing unit and the sensor are constructed for bi-directional communication between the external controller and each one of the dosing unit and the sensor.

U.S. Pat. No. 5,584,688, to Sakuma, et al., entitled "Medicine injection device," describes a medicine injection device capable of continuously administrating a medicine to the body of a patient over a long period of time while keeping the patient from being restrained during administration. The medicine injection device includes a medicine container and at least one medicine passage each arranged in at least one of a root and a crown, so that a medicine stored in the medicine container is administrated through the medicine passage to the body of a patient.

U.S. Pat. No. 5,614,223, to Sipos, entitled, "Intraoral medicament-releasing device," describes controlled rate-release devices for releasing a pharmaceutically active agent into the oral cavity by the dissolving action of the saliva, a process of preparing such devices and methods of preventing/treating conditions/diseases in a mammal by delivering a pharmaceutically active substance into the oral cavity.

U.S. Pat. No. 5,686,094, to Acharya, entitled, "Controlled release formulations for the treatment of xerostomia," describes controlled or sustained dosage forms, and in particular certain polymeric matrices or complexes which are suitable for achieving controlled or sustained delivery of an active composition. The compositions are especially useful for local, parenteral, buccal, gingival, and oral controlled release of active compositions, such as pharmaceuticals, and take the form of granules, encapsulated capsules, tablets, chewable gums, ingestible and implantable boluses, candies, lolipops, pourable liquids, gels, suppositories and the like.

U.S. Pat. No. 5,869,096, to Barclay, et al., entitled "Oral osmotic device with hydrogel driving member," describes an osmotic device for delivering a drug, such as an anti-fungal, into the mouth of a human patient is disclosed. The device comprises a wall surrounding a compartment housing a layer of an agent that is insoluble to very soluble in aqueous biological fluids, e.g., saliva, and a layer of a fluid swellable, hydrophilic polymer. A passageway in the wall connects the agent with the exterior of the device. The wall is permeable to the passage of aqueous biological fluid but substantially impermeable to the passage of the hydrophilic polymer.

U.S. Pat. No. 7,699,834, to Hood, et al., entitled "Method and system for control of osmotic pump device," describes a system including a remotely controlled osmotic pump device and associated controller. According to some embodiments, an osmotic pump device is placed in an environment in order to pump a material into the environment or into an additional fluid handling structure within the osmotic pump device. In selected embodiments, a magnetic field, an electric field, or electromagnetic control signal may be used.

US Patent Application Publication No. 20060115785, to Li, et al., entitled "Systems and methods for intra-oral drug delivery," describes systems and methods for intra-oral delivery of drugs. For dental diseases, the system is placed so that release of the therapeutic agent occurs in the immediate vicinity of the disease process.

US Patent Application Publication No. 20040147906, to Voyiazis, et al., entitled "Implantable interface system," describes an oral implant including one or more chambers capable of containing materials delivered and/or receiving materials extracted by the implant. Micro- and nano-mechanical and electro-mechanical components, such as microfluidic pumps, perform the mechanics of the delivery and/or extraction of material via the oral implant. Communications means, including wireless communications, associated with the oral implant allow for remote control of the implant and/or remote reporting of information associated with the implant, such as test results.

US Patent Application Publication No. 20020133120, to Yeh, entitled "Light, thin, and flexible medication infusion apparatuses attachable to user's skin and watch type monitor and controller," describes apparatuses having multiple reservoir cells, a pump, a pump controller, one or more batteries on a flexible pad so that the apparatuses may be adhesive to the user's skin as a big and thick Band-Aid.

U.S. Patent Application Publication No. 20040147906, to Voyiazis et al., entitled "Implantable Interface System", describes an oral implant that may include a micro-pump or nano-pump for extracting or delivering material to the body of the patient.

In the light of above discussion, systems, methods and devices are desired that provide for controlled rate of drug release for extended period of times to cure chronic diseases.

SUMMARY

Embodiments of the invention disclose a system for controlled oral drug delivery. The system may comprise a removable device comprising a drug to be delivered, wherein the drug is delivered based on osmotic pressure generated in the removable device, a receptacle to hold the removable device in an oral cavity, and a base station configured to dock the removable device for determining information about one or more characteristics of the removable device.

Embodiments of the invention disclose a system for controlled oral drug delivery. The system may comprise: a removable device comprising a drug to be delivered, wherein the drug is delivered based on osmotic pressure generated in the removable device; a receptacle to hold the removable device in an oral cavity; a base station configured to dock the removable device for determining information about one or more characteristics of the removable device; and an assistive tool configured to enable insertion and removal of the removable device into and from the receptacle.

Embodiments of the invention disclose a removable device for controlled oral drug delivery. The removable device comprising a housing for removable insertion into an oral cavity, the housing comprising: a drug chamber comprising a drug to be delivered; and an osmotic chamber comprising an osmotic agent enclosed by a flexible barrier membrane on a first end and an osmotic membrane at a second end, wherein the flexible barrier membrane separates the osmotic chamber from the drug chamber and the osmotic membrane interfaces with saliva, and wherein the flexible barrier membrane is actuated by osmotic pressure in the osmotic chamber to deliver the drug from the drug chamber.

Embodiments of the invention disclose a system for controlled oral drug delivery. The system comprising: a removable device comprising a drug to be delivered and an osmotic agent, wherein pressure generated in the osmotic agent actuates the removable device to deliver the drug; a receptacle to hold the removable device in an oral cavity; and a base station configured to: dock the removable device for determining information about one or more characteristics of the removable device; and communicate the information to an external telemedical device.

Embodiments of the invention provide a system for controlled release of a drug. The system comprises a removable drug-containing cartridge that works on the principle of osmosis, a receptacle that holds the cartridge and a base station. The base station includes a provision for docking the cartridge. Also, base station helps in identification of the cartridge, determination of the level of the drug in the cartridge and communication of the cartridge with a telemedical service station. The receptacle is inserted into an oral cavity of a subject that in turn provides for the insertion of the cartridge into the oral cavity since the receptacle holds the cartridge.

Embodiments of the invention provide a system for controlled drug release, comprising: a removable drug-containing cartridge; a receptacle to hold the cartridge; a base station for: docking the cartridge; identification of the cartridge, determination of cartridge fill level, and communication of the cartridge with a telemedical service; an assistive tool to help a user in insertion and removal of the cartridge into and from the receptacle. The assistive tool also helps in insertion and removal of the cartridge into and from the base station. The receptacle is being adapted for insertion into an oral cavity of a subject that further adapts for insertion of the cartridge into the oral cavity.

Further, the embodiments of the invention provide a system for controlled drug release, where the system comprises a drug containing cartridge working on the osmosis principle, a receptacle holding the cartridge, a base station and an assistive tool. The base station helps in a number of ways, including, holding the cartridge, identification of the cartridge, determination of the drug level in the cartridge and communication of the cartridge with a telemedical service station. The assistive tool helps a user for inserting and removing the cartridge into and from the receptacle and also for inserting and removing a cartridge into and from the base station. The drug contained in the cartridge is selected from the group consisting of anti-movement disorder agents. The receptacle is being adapted to be inserted into an oral cavity of a patient.

Embodiments of the invention provide a device for controlled drug release comprising a drug containing cartridge, a receptacle to hold the cartridge, and a dental appliance to hold the receptacle. The dental appliance is selected from the group consisting of a removable denture, a prosthetic tooth crown, a dental bridge, a moral band, a bracket, a mouth guard, a night guard and a dental implant.

An aspect of the invention provides the removable cartridge that further includes at least one or more single chamber osmotic pump. Every osmotic pump is actuated by the principle of osmosis. The single chamber may include a solid drug or a liquid drug. The cartridge, further, comprises an osmotic membrane that separates the drug contained in the single chamber from the saliva in the mouth, but allows water from the saliva to enter into the chamber. This happens due to concentration gradient created across the osmotic membrane. This process creates an osmotic pressure in the single chamber. The cartridge further comprises an outlet through which the drug is expelled out from the single chamber after being dissolved in the water and being pushed out from the chamber by the osmotic pressure.

A further aspect of the invention provides the removable cartridge including at least one or more double chambers osmotic pump. The first chamber is filled with a hygroscopic material selected from the group consisting of solid salt, saccharides, hydrogels, and polymers. The second chamber is filled with a liquid drug. The cartridge further comprises osmotic membrane separating saliva in mouth from the hygroscopic material contained in the first chamber, but allowing water from saliva to enter the first chamber due to concentration gradient created across the osmotic membrane and also generating an osmotic pressure. Furthermore, the cartridge comprises a barrier, selected from the group consisting of flexible membranes and pistons, separating the first and second chambers from each other and that deflects when acted upon by the osmotic pressure generated in the first chamber and pushes (or applies a force on) the drug from the second chamber. The cartridge also comprises an outlet through which the liquid drug is expelled out from the second chamber upon being pushed (forced) by the deflection in the barrier.

According to another aspect of the invention, each of the drug-containing cartridge and receptacle include one or more magnets or magnetisable material that aimed at facilitating the insertion and retention of the cartridge into the receptacle by mutual magnetic attraction.

According to another aspect of the invention, the receptacle is attached to a dental appliance, the dental appliance being selected from the group consisting of a removable denture, a prosthetic tooth crown, a dental bridge, a moral band, a bracket, a mouth guard, a night guard and a dental implant.

According to another aspect of the invention, the removable drug-containing cartridge includes an identification tag, selected from the group consisting of Radio Frequency Identification (RFID) and bar codes that provide for specific identification of the cartridge.

According to another aspect of the invention, for the purpose of determination of cartridge fill level, the base station includes one or more light sources, for example Light Emitting Diodes (LEDs) and a photodiode situated opposite to the LEDs in the base station. In case of a single chamber cartridge, one LED and one receiving photodiode is used. Initially, the chamber is filled with solid drug that blocks the light beam from the LED to reach the photodiode. As a result, no light is received by the receiving photodiode. Further, when the drug becomes dissolved due to usage, the light beam may penetrate the cartridge and is received by the receiving photodiode.

In case of a two-chamber cartridge, one chamber includes a salt while the other includes a liquid drug. Further, the salt chamber also includes a dye that gets dissolved in the water and forms a dyed salt solution. In the base station, two light sources, e.g., LEDs and one receiving photodiode are situated. Initially, before the usage, the light beams of both LEDs may penetrate the cartridge and are received by the receiving photodiode. After/during usage, the barrier of the cartridge is deflected. As a result, one LED beam is blocked by the membrane and absorbed by the dyed salt solution contained in the salt chamber. The second LED light beam penetrates membrane or dye and is always received by the photodiode and may serve as a reference. In this way, the fill level may be determined based on the light beams received at the receiving photodiode.

According to another aspect of the invention, the base station provides for emitting two or more light beams of different wave length using two or more LEDs and directed to one or more opposite photodiodes. The wavelengths are chosen in a way that the first light beam may penetrate the cartridge without being absorbed by dye contained in the cartridge. This shows that the dye is not suspended and diluted in the liquid drug and hence, cartridge is empty of liquid drug. The other light beams are absorbed at different absorption levels depending upon the concentration of the dye in the chamber of cartridge, which reflects the amount of drug remaining in the chamber.

According to another aspect of the invention, the base station is adapted to provide communication between the removable drug containing cartridge and a monitoring and supervising center, and thus includes a communication protocol, for example, ZigBee or Bluetooth, providing for transmitting relevant acquired information, such as the cartridge identification and fill level, to a mobile gateway, such as a mobile telephone, with the purpose of forwarding the relevant acquired information to a remote monitoring and supervising center.

According to another aspect of the invention, the system includes an assistive tool to help a user in the insertion and removal of the cartridge into and from the receptacle and into and from the base station.

According to another aspect of the invention, the assistive tool includes one or more (electro-) magnets aimed at facilitating the attachment of the assistive tool to the cartridge to help the user in the manipulation of the cartridge.

According to an additional aspect of the present invention, a device that is adapted to be removably inserted to an oral cavity of the subject is provided.

According to an alternative aspect of the present invention, a device is adapted to be permanently inserted to the oral cavity of the subject. The device is for controlled drug release includes a removable drug containing cartridge, a receptacle to hold the cartridge, a dental appliance to hold the receptacle. The cartridge being actuated by an osmotic pumping principle. The dental appliance may be selected from a group consisting of a removable denture, a prosthetic tooth crown, a dental bridge, a moral band, a bracket, a mouth guard, a night guard and a dental implant.

According to an additional aspect of the present invention, the device is adapted to be permanently inserted to the oral cavity of the subject, and the device further includes a removable component, which houses at least one drug reservoir and the power source.

According to another aspect of the present invention, there is provided a method of controlled drug release. The method includes providing a device for controlled drug release, which comprises a reservoir containing a drug. Further, the method includes supporting the device in an oral cavity of a subject, on a dental implement, designed for insertion to the oral cavity of a subject and for supporting said device.

Other systems, methods, features, and advantages of the present invention will be or become apparent to one with skill in the art upon examination of the following drawings and detailed description.

BRIEF DESCRIPTION OF THE DRAWINGS

Figure 1:
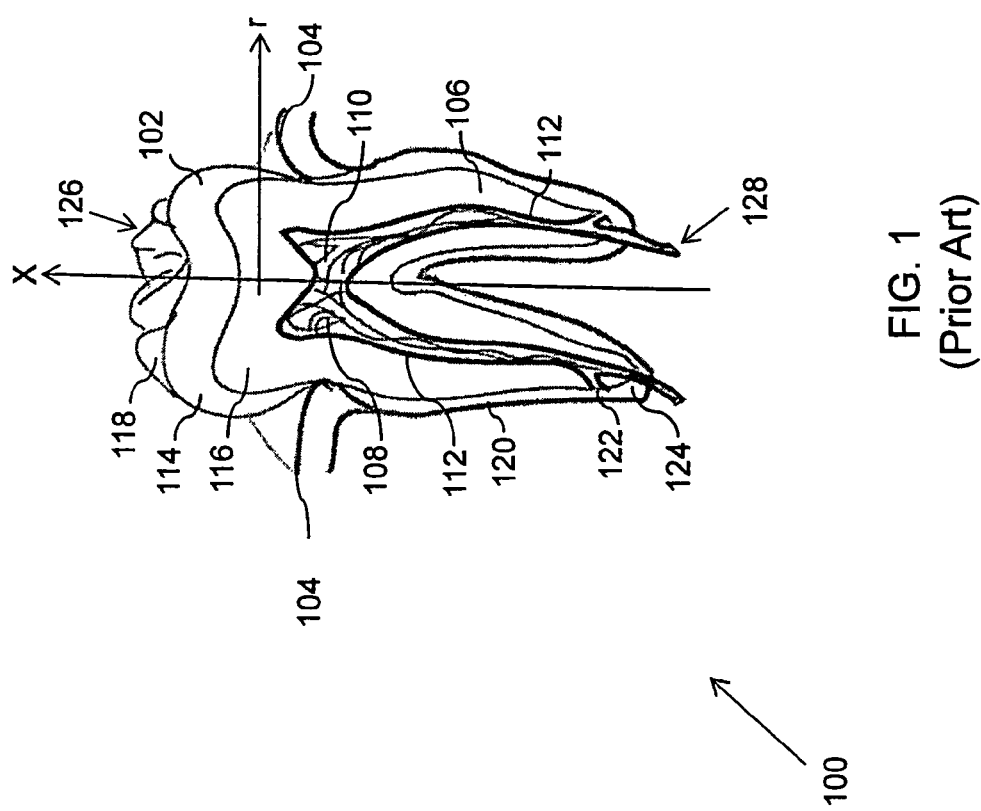
Figure 2G:
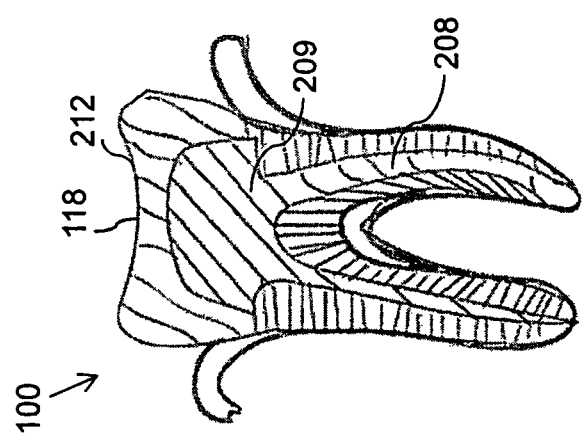
Figures 3A, 3B:
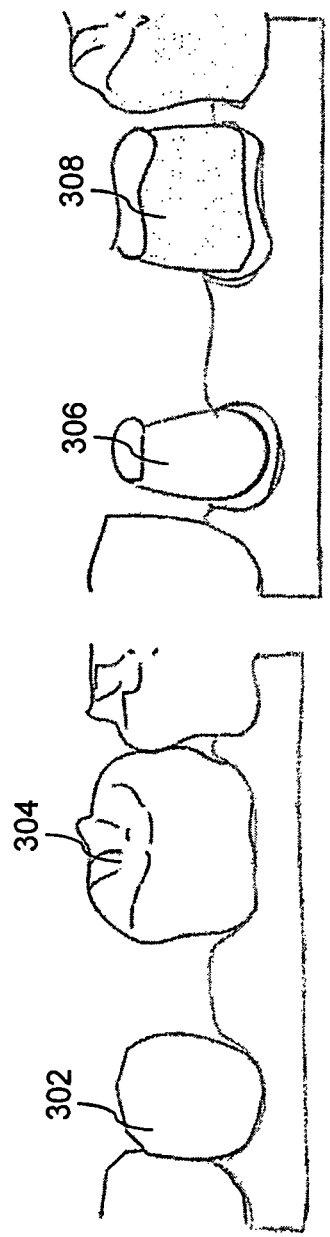
Figures 3C, 3D:
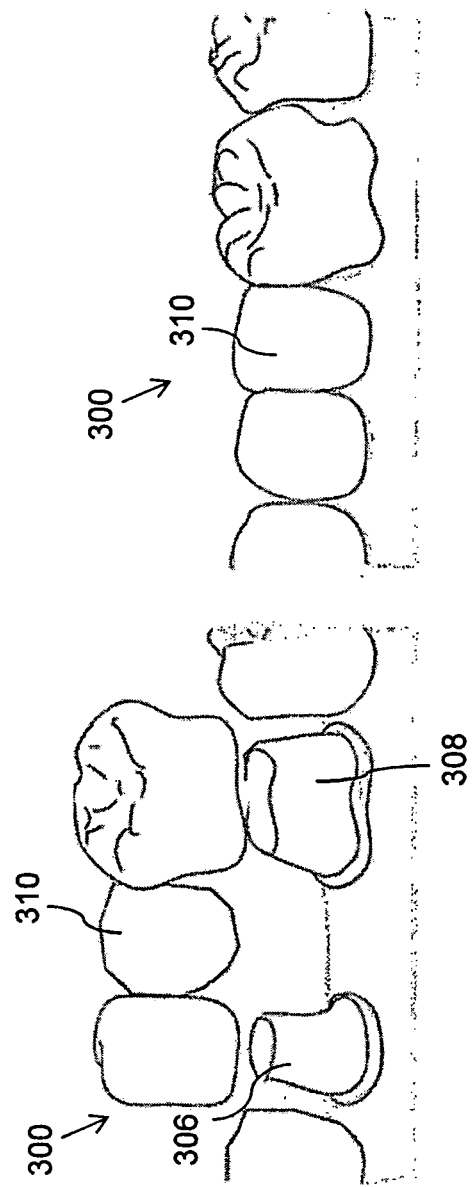
Figure 4B:
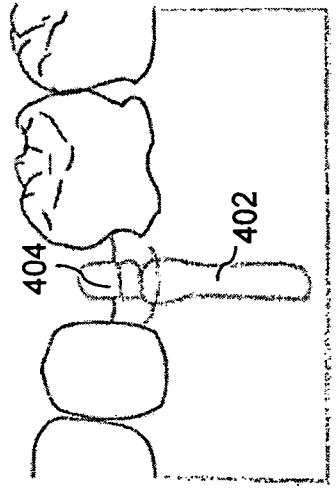
Figure 4A:
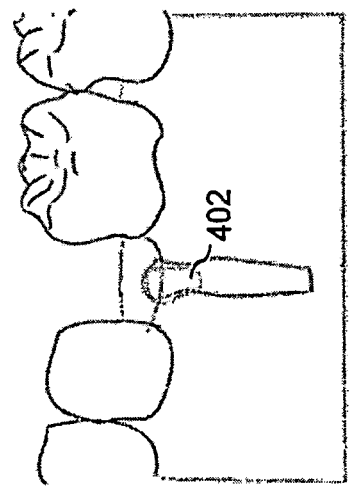
Figure 4C:
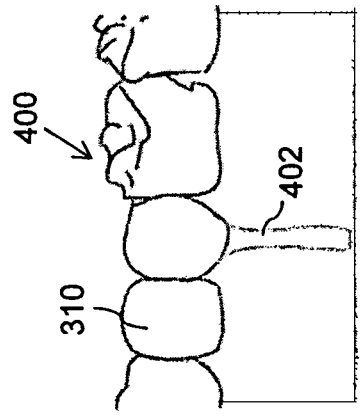
Figure 5B:
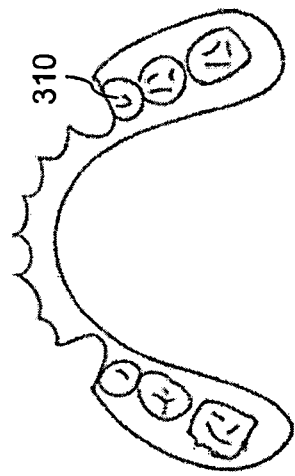
Figure 5C:
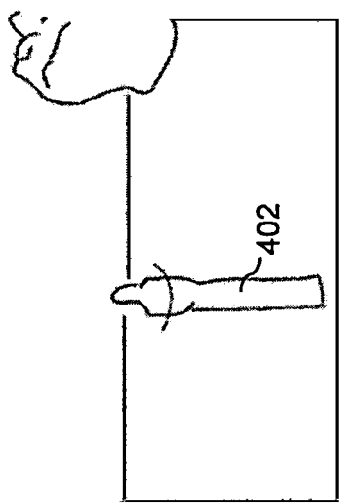
Figure 5A:
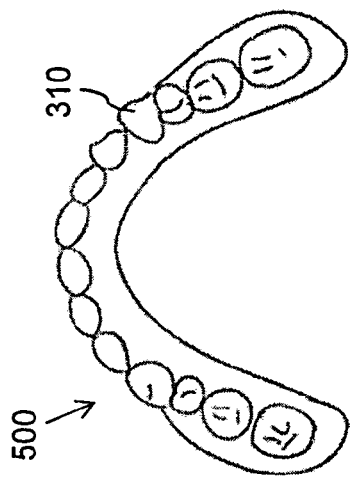
Figure 6C:
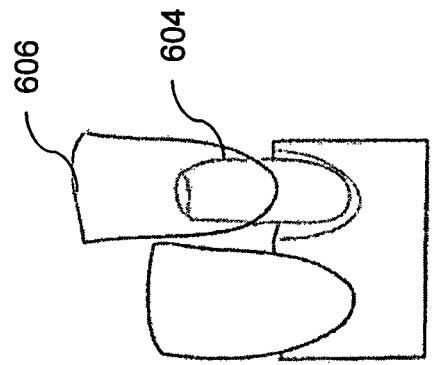
Figure 6B:
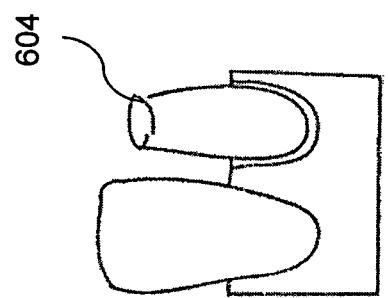
Figure 6A:
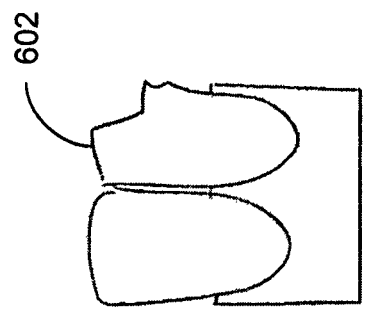
Figures 7A, 7B, 7C:
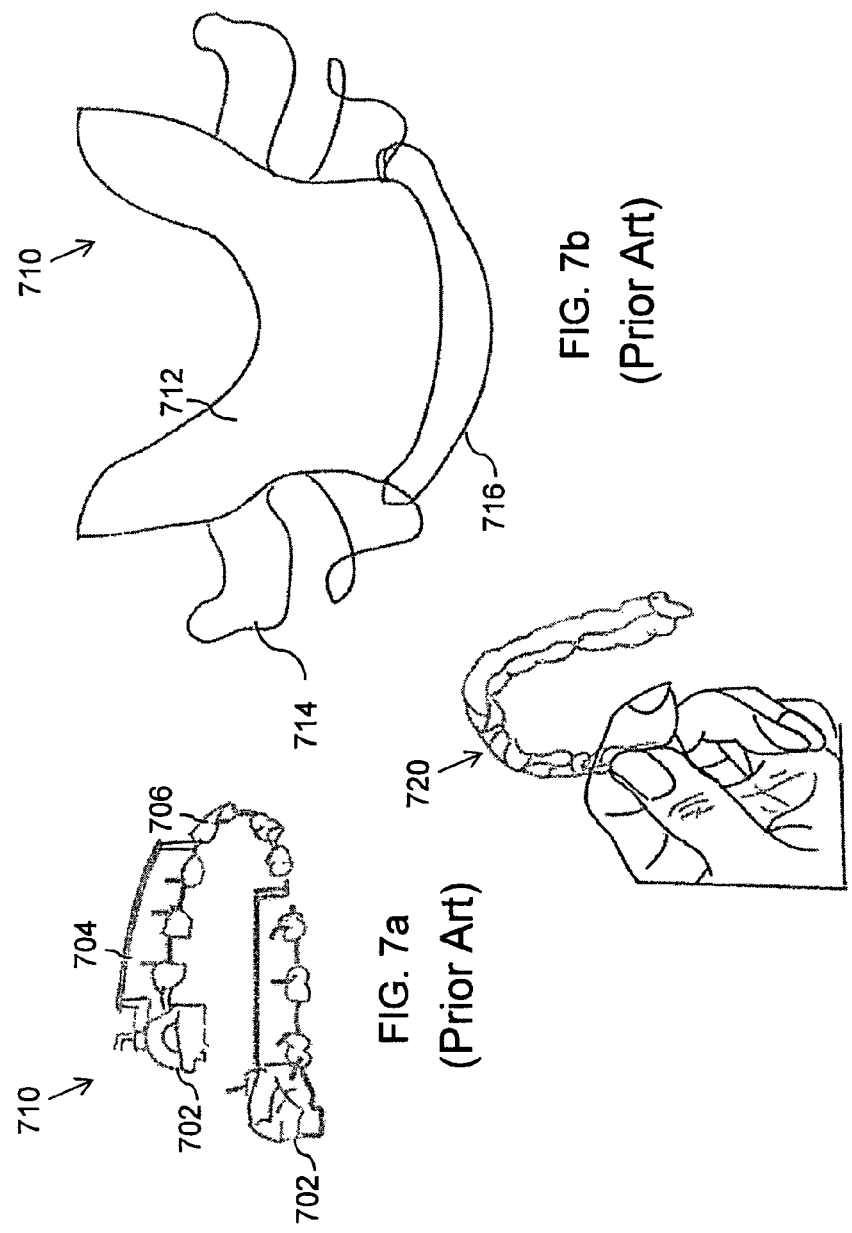
Figure 8:
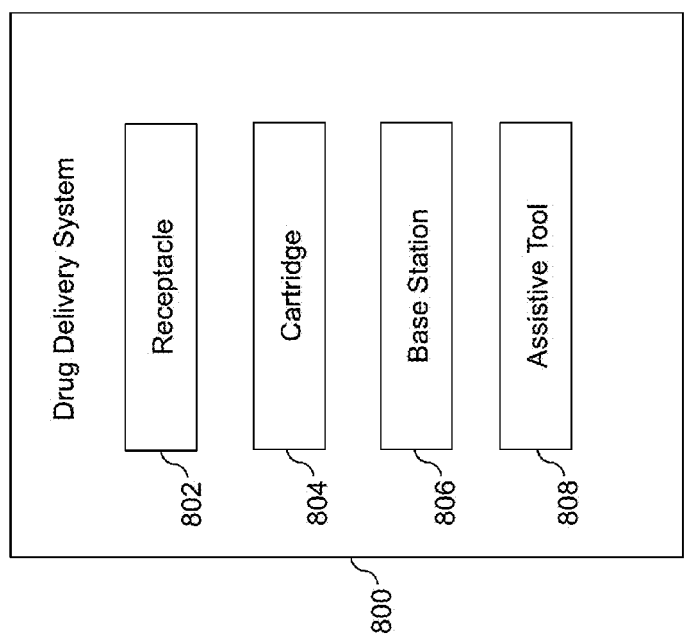
Figure 9:
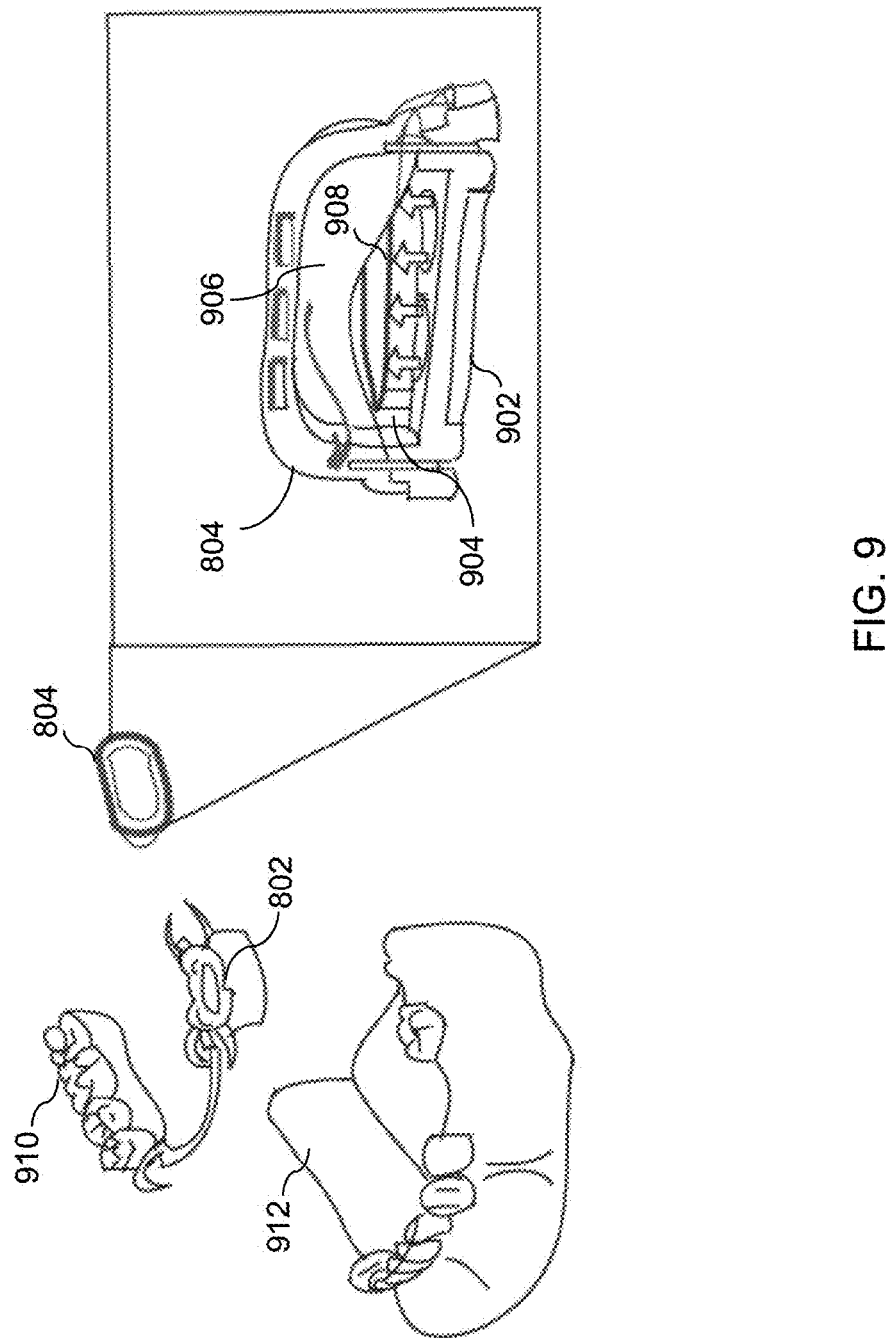
Figure 10A:
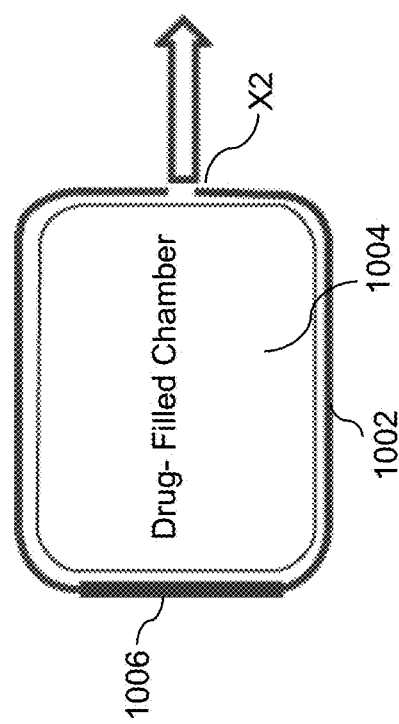
Figure 10B:
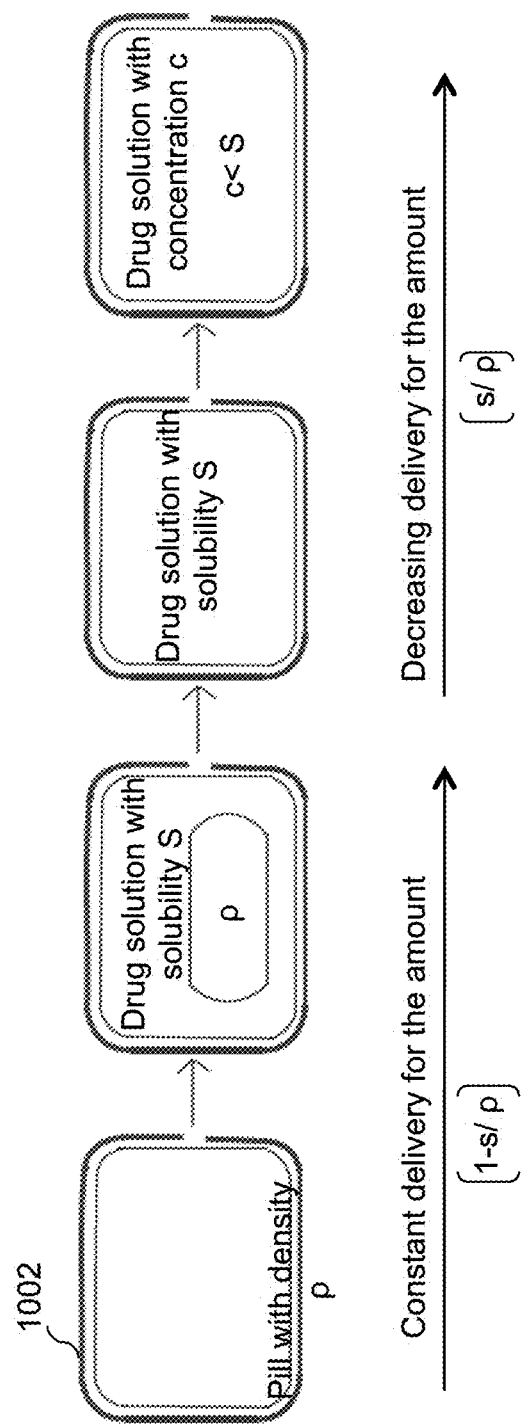
Figure 11A:
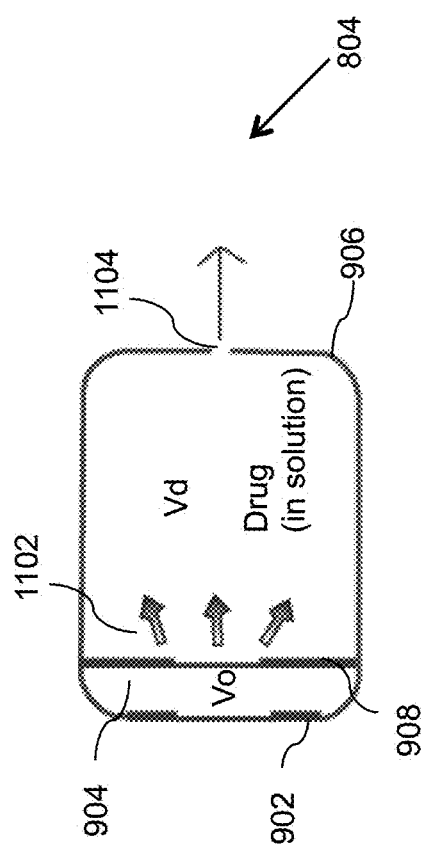
Figure 11B:
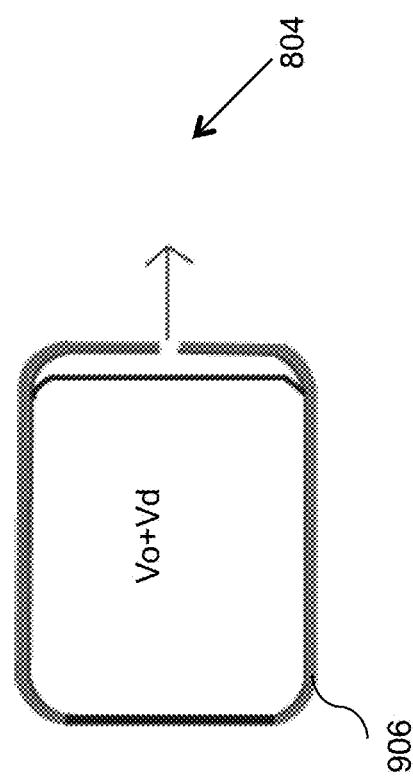
Figure 13:
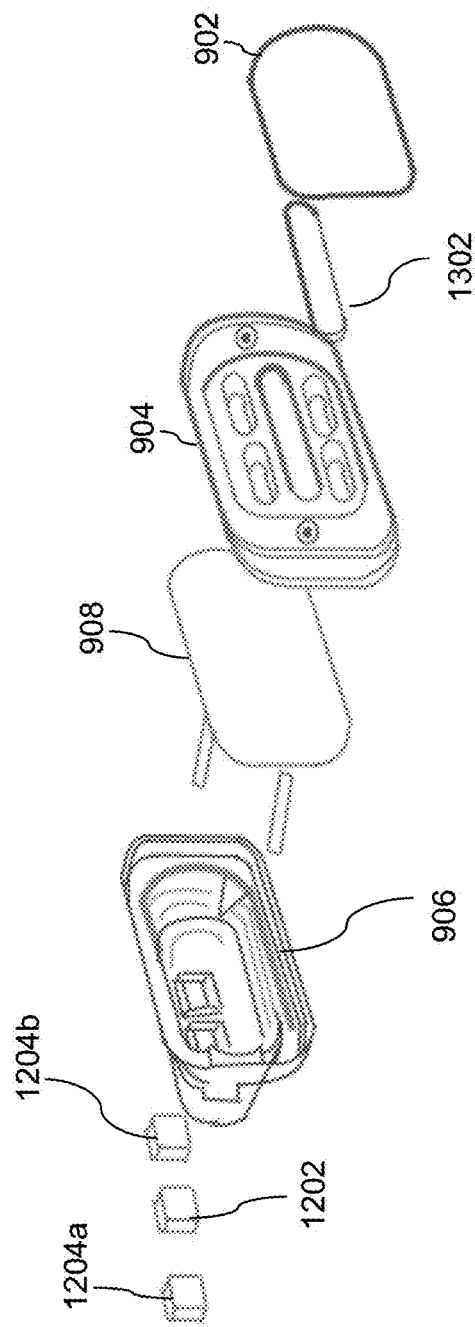
Figure 14A:
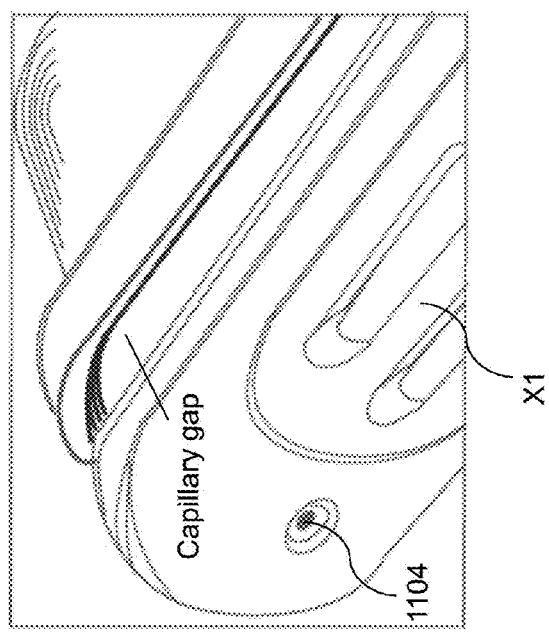
Figure 14B:
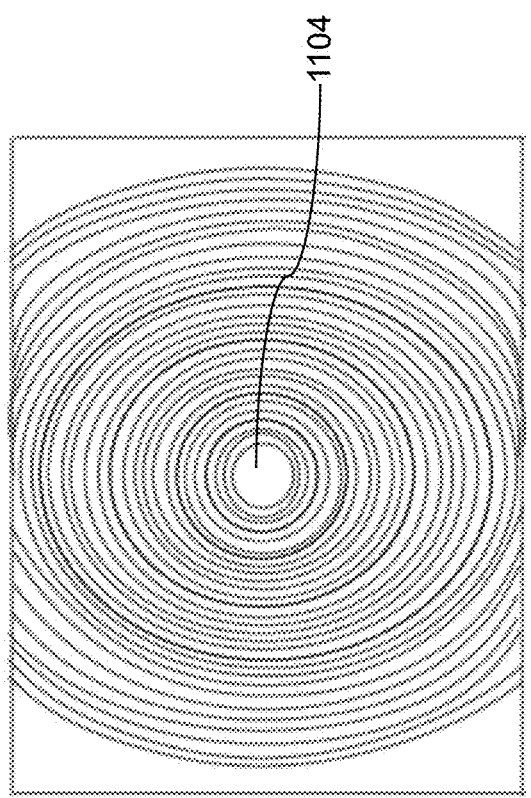
Figure 15B:
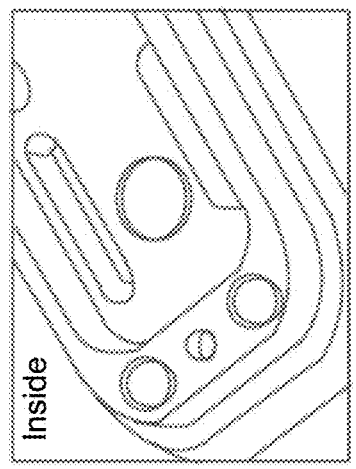
Figure 15A:
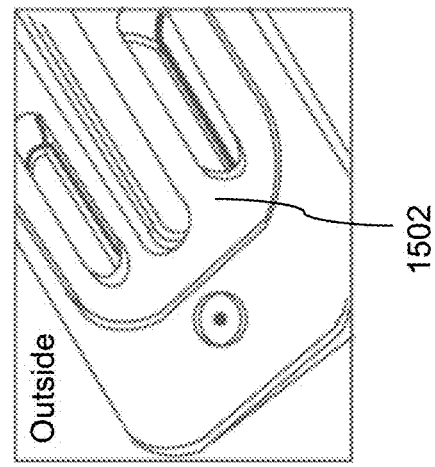
Figure 16B:
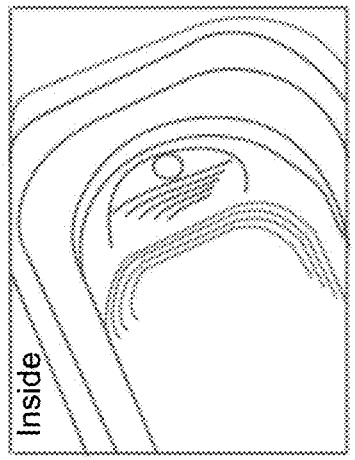
Figure 16A:
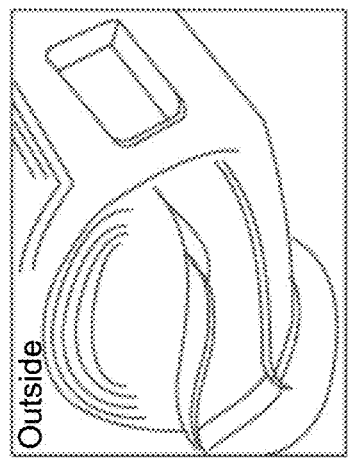
Figure 17:
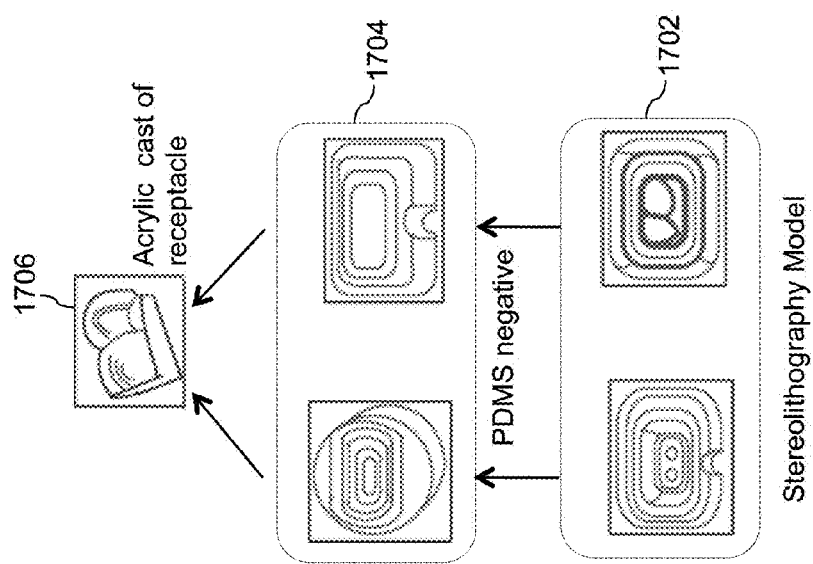
Figure 18:
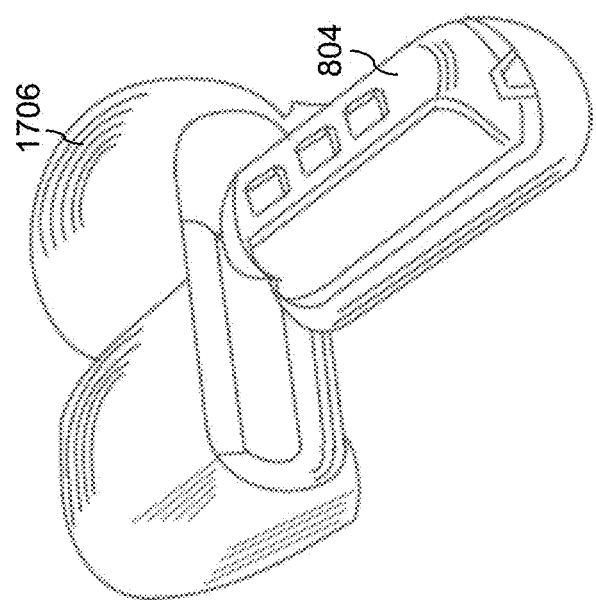
Figure 19A:
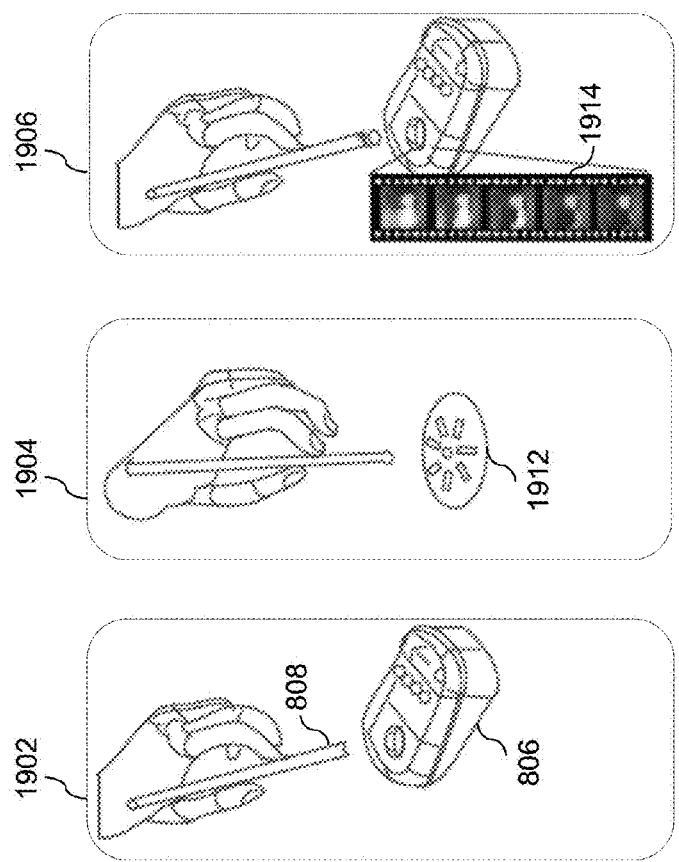
Figure 19B:
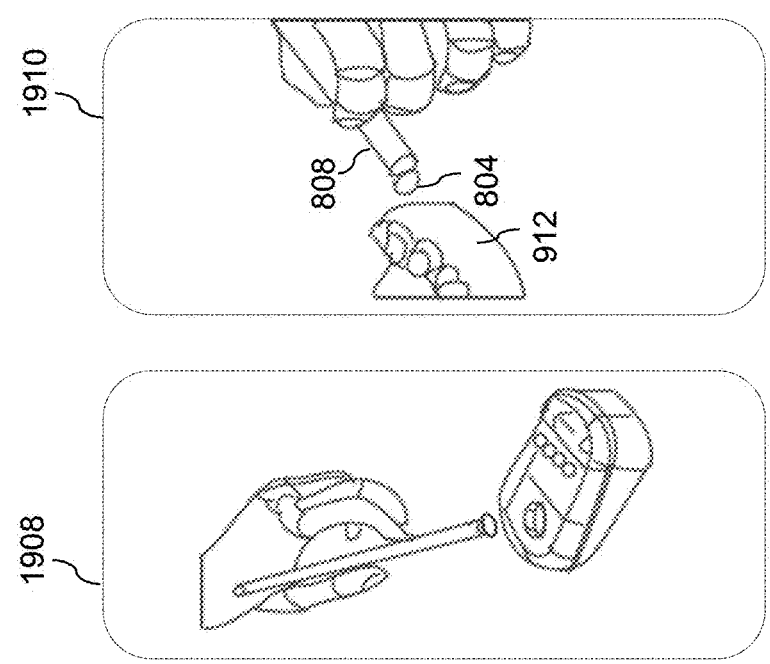
Figure 20:
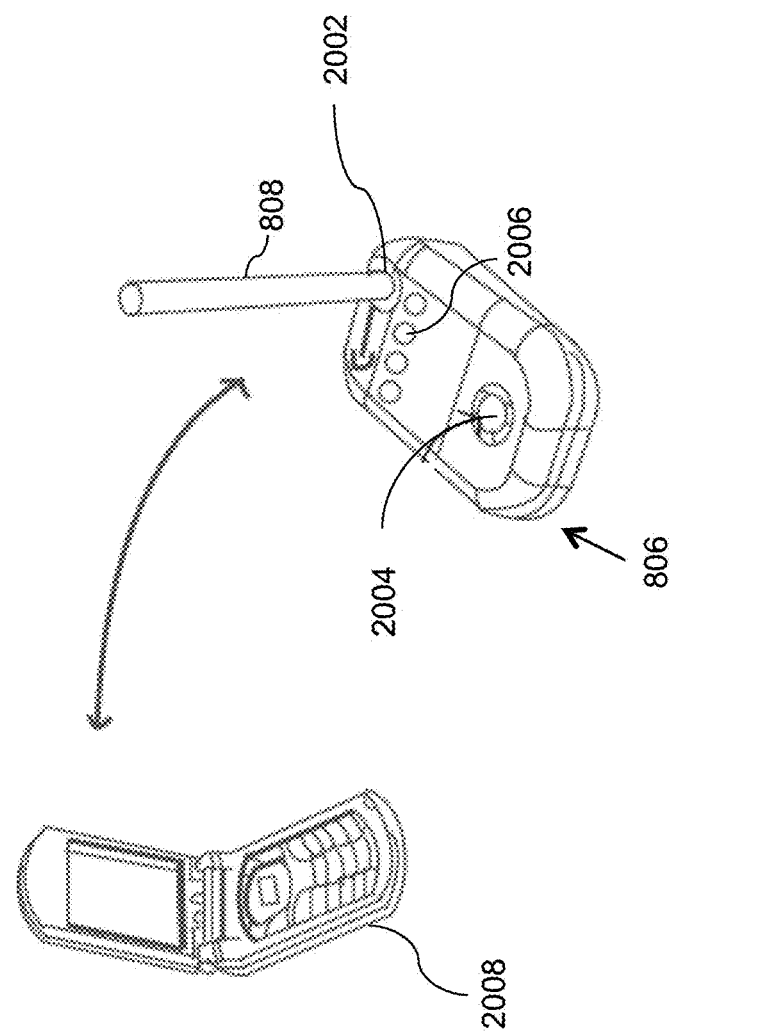
Figure 21:
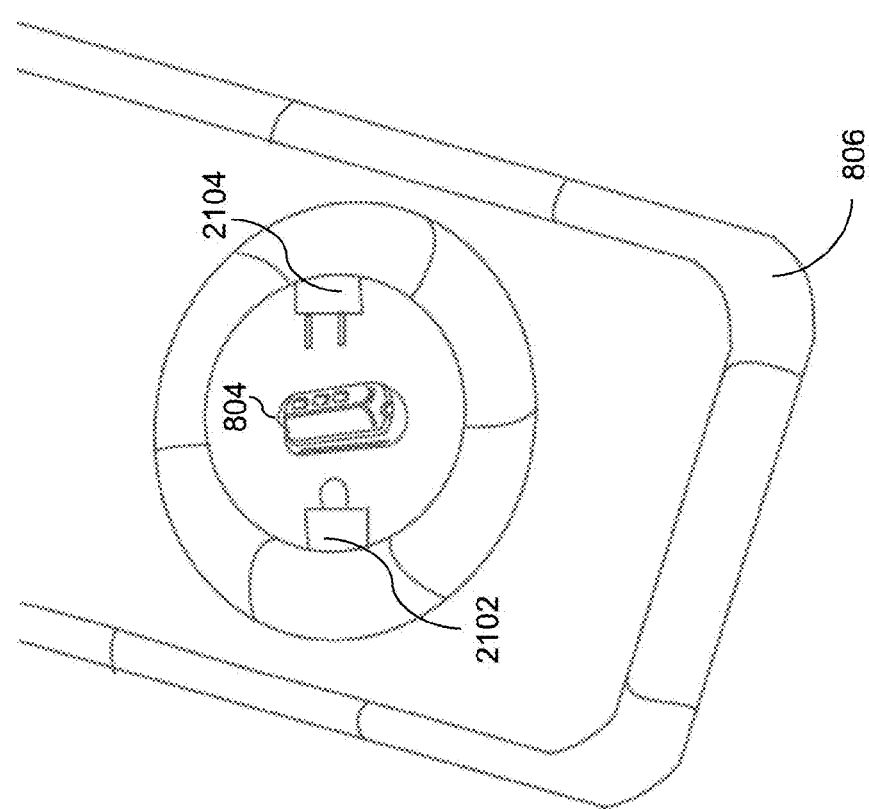
Figure 22:
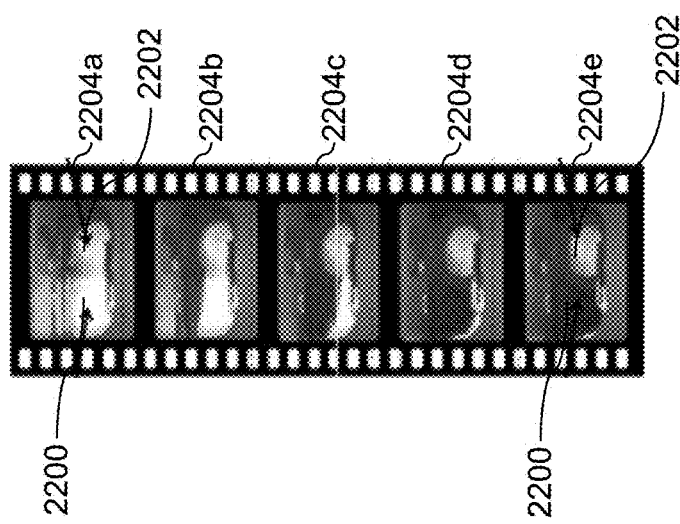
Figures 23A, 23B:
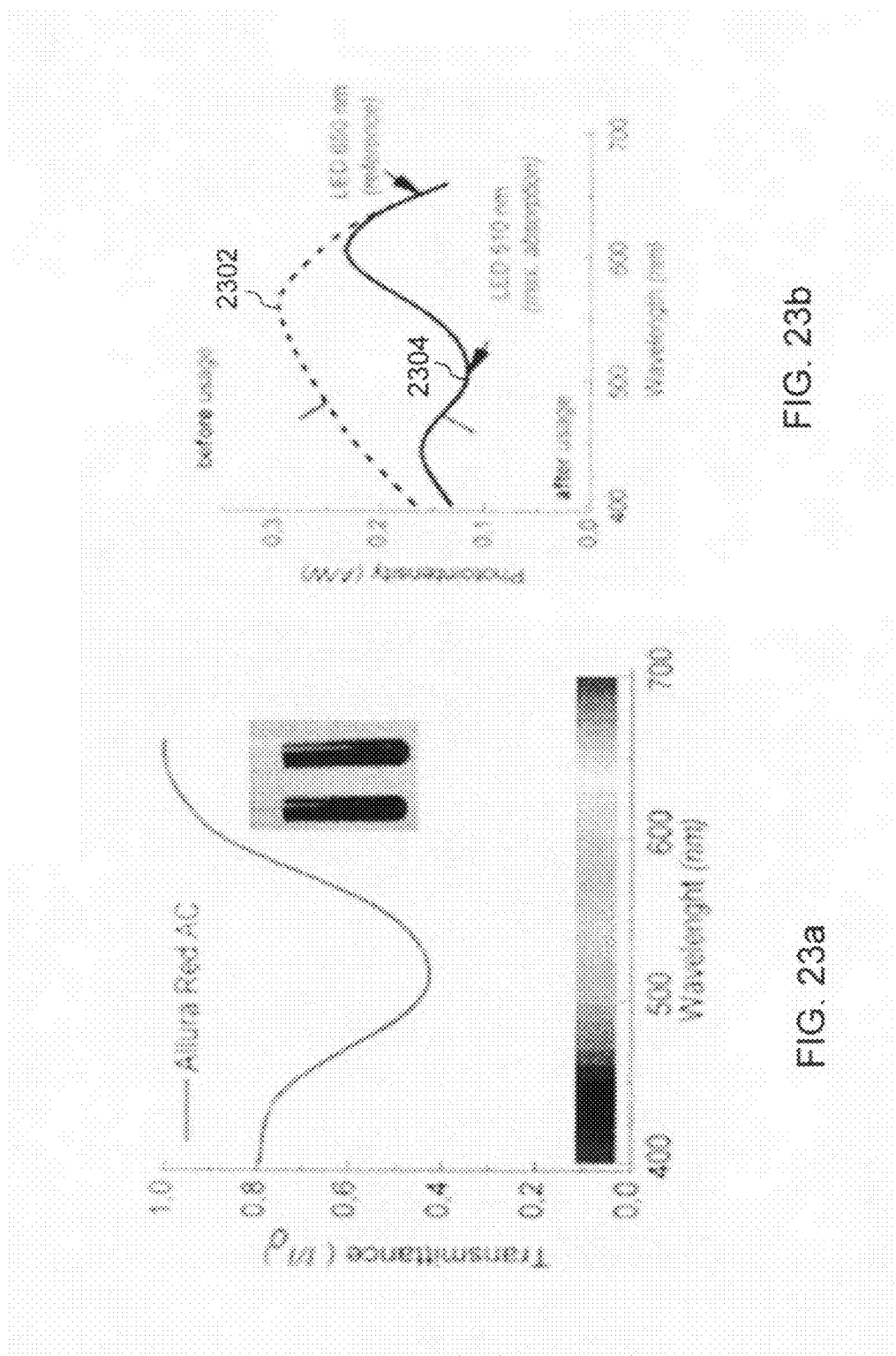
Figure 24A:
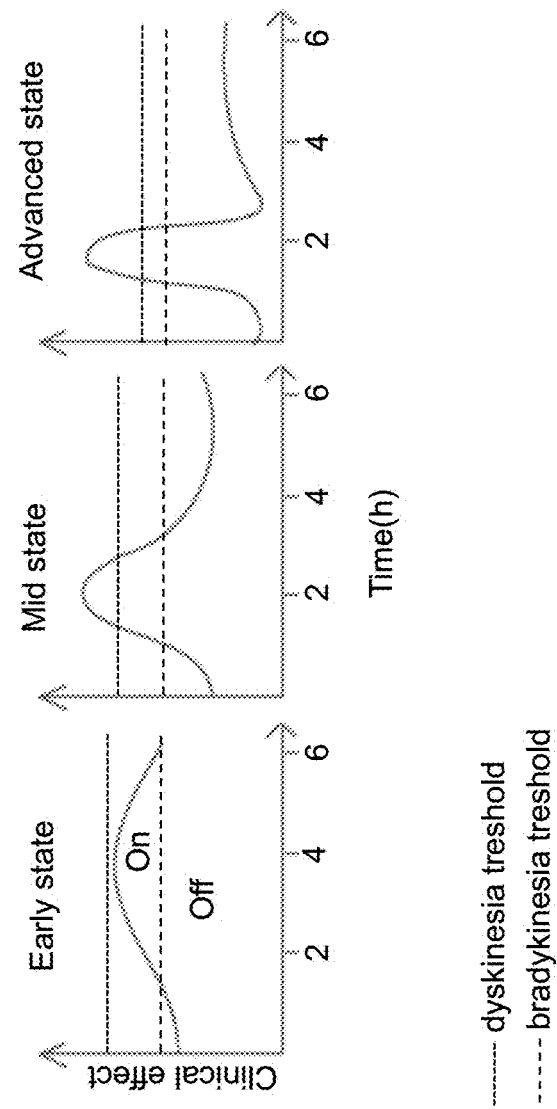

Having thus described the invention in general terms, reference will now be made to the accompanying drawings, which are not necessarily drawn to scale, and wherein:

FIG. 1 is a cross-sectional view of a tooth, as known;

FIGS. 2A to 2G schematically illustrate generally known steps in root canal therapy;

FIGS. 3A to 3F schematically illustrate generally known application of a dental bridge;

FIGS. 4A to 4C schematically illustrate generally known application of a dental implant;

FIGS. 5A to 5C schematically illustrate generally known dentures;

FIGS. 6A to 6C schematically illustrate generally known application of a dental crown;

FIGS. 7A to 7C schematically illustrate generally known braces;

FIG. 8 is a block diagram illustrating various components of a drug delivery system, in accordance with an embodiment of the invention;

FIG. 9 illustrates application of a cartridge of the drug delivery system in a partial removable prosthesis, in accordance with an embodiment of the invention;

FIGS. 10A and 10B illustrate a single-chamber cartridge and its functioning respectively, in accordance with an embodiment of the invention;

FIGS. 11A and 11B illustrate functioning of a double-chamber cartridge, in accordance with an embodiment of the invention;

FIGS. 12A and 12B illustrate a front view and a back view respectively of the cartridge, in accordance with an embodiment of the invention;

FIG. 13 illustrates an exploded view of the cartridge, in accordance with an embodiment of the invention;

FIGS. 14A and 14B illustrate an outer surface of the cartridge, in accordance with an embodiment of the invention;

FIG. 15A illustrates a magnified view of an osmotic reservoir from outside the cartridge (that directly interfaces with the external environment, such as saliva), in accordance with an embodiment of the invention;

FIG. 15B illustrates a magnified view of the osmotic reservoir from inside the cartridge (that directly interfaces with the osmotic agent), in accordance with an embodiment of the invention;

FIG. 16A illustrates a magnified view of a drug reservoir from outside the cartridge (that directly interfaces with the external environment, such as the receptacle), in accordance with an embodiment of the invention;

FIG. 16B illustrates a magnified view of the drug reservoir from inside the cartridge (that directly interfaces with the drug), in accordance with an embodiment of the invention;

FIG. 17 illustrates the stages in preparation of the receptacle as part of a partial removable prosthesis, in accordance with an embodiment of the invention;

FIG. 18 illustrates an integrated receptacle with a cartridge, in accordance with an embodiment of the invention;

FIGS. 19A and 19B illustrate various stages of using an assistive tool, in accordance with an embodiment of the invention;

FIG. 20 illustrates a base station, in accordance with an embodiment of the invention;

FIG. 21 illustrates fill level measurement method of the cartridge, in accordance with an embodiment of the invention;

FIG. 22 illustrates exemplary stages during use of a double-chamber cartridge, in accordance with an embodiment of the invention;

FIG. 23A illustrates transmittance spectrum of Allura Red AC;

FIG. 23B illustrates theoretical sensor signal of a used and an unused cartridge;

FIG. 24A illustrate motor fluctuations in a standard Parkinson therapy; and

Figure 24B:
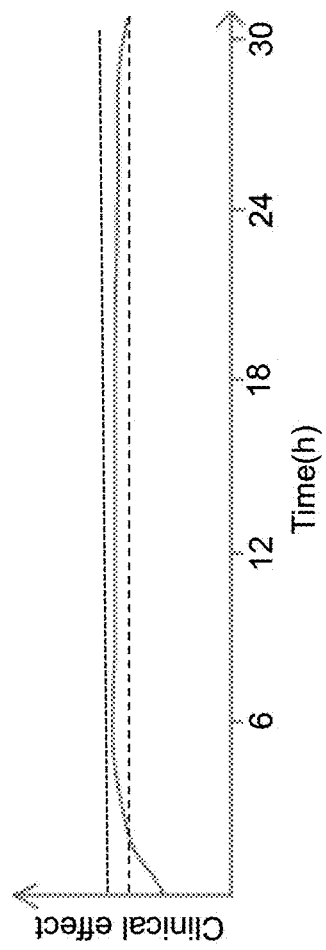

FIG. 24B illustrate motor fluctuations in aimed drug profile with the system and method of the present invention.

DETAILED DESCRIPTION OF THE INVENTION

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

With reference to FIG. 8, a block diagram of various components of a drug delivery system 800 are illustrated, in accordance with an embodiment of the invention. Generally, advanced stages of disorders such as Parkinson's disease require invasive administration of drugs into the bloodstream, for e.g., by subcutaneous pumps or duodenal catheters. Drug Delivery system 800 is aimed to be a far less invasive intraoral system for the self-medicated treatment of Parkinson's disease. Drug delivery system 800 provides constant release of drug to the buccal mucosa and consequently into the bloodstream, thereby avoiding first-pass metabolism or acts as a continuous enteral infusion pump (e.g. for Levodopa).

Drug delivery system 800 may include a device for controlled release of drug in an oral cavity of a user. The device may include a receptacle and a removable device, such as receptacle 802, a removable device 804 (hereinafter referred to as cartridge 804), and a dental appliance to hold the receptacle (not shown). Further, the system includes a base station 806 and an assistive tool 808. The drug to be delivered is contained in cartridge 804, and the cartridge may be attached to the receptacle 802. The receptacle 802 may be formed at the jaw of a patient. In an embodiment of the invention, cartridge 804 and receptacle 802 may include one or more magnets to keep them attached.

Cartridge 804 operates based on osmotic principle and therefore, may not require external means to actuate or deliver the drug. For example, cartridge 804 may include one or more chambers containing drugs. Cartridge 804 is discussed in detail in conjunction with FIGS. 10 and 11. Further, cartridge 804 may be removed from the receptacle 802 by using assistive tool 808. Moreover, assistive tool 808 may be used to insert cartridge 804 in base station 806. In an embodiment of the invention, assistive tool 808 may include one or more magnets to insert and/or remove cartridge 804 from receptacle 802 and base station 806. In another embodiment of the invention, one or more of assistive tool 808, receptacle 802 and/or cartridge 804 may include magnetizable steel.

Base station 806 may be used to detect the level of drug in cartridge 804. Further, base station 806 may communicate with telemedical services. For instance, therapeutically relevant information like compliance with the therapy plan and medication may be acquired, that may be further, analyzed and transmitted via a mobile gateway to a point of care unit by base station 806.

FIG. 9 illustrates application of cartridge 804 of the drug delivery system 800 in a partially removable prosthesis 910, in accordance with an embodiment of the invention. As shown, receptacle 802 may be formed on prosthesis 910. Prosthesis 910 may be applied to a jaw 912 of the patient. However, a person skilled in the art will appreciate that the prosthesis may be fully removable based on the requirement of the patient.

The enlarged sectional FIG. 9 illustrates internal parts of cartridge 804. As shown, cartridge 804 has a housing forming the body of cartridge 804, which includes an osmotic membrane 902 (hereinafter referred to as semi-permeable membrane 902) that forms a barrier between an osmotic chamber or reservoir 904 and saliva or other fluids in the mouth of the patient. Osmotic reservoir 904 includes an osmotic agent for providing osmotic effect/actuation. Examples of the osmotic agent include hygroscopic material such as solid salt, saccharides, hydrogels, and polymers etc. A drug chamber or reservoir 906 contains the drugs/medicine to be provided to the patient. Further, cartridge 804 includes a barrier/flexible barrier membrane 908 that forms a barrier between the osmotic reservoir 904 and drug reservoir 906. Therefore, cartridge 804 is actuated by osmotic actuation mechanism and does not require any external actuation. As shown in this FIG. 9, cartridge 804 contains a two-chamber design (i.e. a single osmotic reservoir 904 and a single drug reservoir 906). However, cartridge may include a single chamber or multiple chamber configurations.

With reference to FIGS. 10A and 10B, a single-chamber cartridge 1002 and its functioning are respectively illustrated. Single-chamber cartridge 1002 acts as an osmotic pump that consists of a single chamber 1004 filled with solid drug. In an embodiment, single chamber 1004 may also include a liquid drug. The drug is separated from saliva of the patient by an osmotic membrane 1006. Further, the cartridge 1002 has a separate outlet 'x2' that provides a way for the drug out of the cartridge 1002.

As shown in FIG. 10B, during operation, water from the saliva enters drug-filled chamber 1004 through osmotic membrane 1006 due to the concentration gradient created across osmotic membrane 1006. This generates an osmotic pressure according to Eq. (1) below:

$$\Pi = S \cdot i \cdot R \cdot T \quad [\text{Eq. 1}]$$

where:

'$\Pi$' is osmotic pressure, 'S' is solubility, 'i' is its Van't Hoff factor, 'R' is the gas constant, and 'T' is temperature.

The generated osmotic pressure pushes the drug solution through the outlet 'x2'. Thereby, the delivery rate, '$\Phi$', of the drug with solubility concentration may be described by Eq. 2, where 'K' is the permeability 'A' is the surface area of the osmotic membrane, '$\Delta\pi$', the osmotic pressure difference between the drug inside the chamber and the osmolality of the saliva and '$\Delta p$', the pressure drop between inside and outside of the cartridge.

$$\Phi = K \cdot A \cdot (\Delta\pi - \Delta p) \quad [\text{Eq. 2}]$$

Constant delivery rates may be achieved as long as the drug is still in saturation. When the last quantity of drug in solid form is solubilised, saturation cannot be maintained any longer and drug concentration within the system will decrease. Thus the amount '$m_{zero}$' of Eq. 3 and FIG. 10B may be released constantly:

$$m_{zero}/m_{total} = 1 - S/\rho \quad [\text{Eq. 3}]$$

Consequently, the delivery rate of the single-chamber design is dependent on the osmotic properties of the drug. Therefore, different drugs will have different delivery rates. To achieve similar delivery rates with different drugs, the properties of the osmotic membrane have to be adapted.

FIGS. 11A and 11B illustrate functioning of a two-chamber/double chamber cartridge 804, in accordance with an embodiment of the invention. Two-chamber cartridge 804 acts as an osmotic pump consisting two-chambers, which are separated by a barrier/flexible barrier membrane 908. The first chamber or osmotic reservoir 904 is filled with an osmotic agent such as solid salt and is separated from saliva by an osmotic membrane 902. The second chamber or drug reservoir/chamber 906 is filled with a drug in liquid form and has a separate outlet 1104.

As shown in FIG. 11A, the volume of osmotic reservoir 904 is designated by '$V_o$,' and the volume of drug reservoir/chamber 906 is designated by '$V_d$'. During operation, water from saliva enters osmotic reservoir 904 due to the concentration gradient across the osmotic membrane 902. The generated osmotic pressure within osmotic reservoir 904 deflects flexible barrier membrane 908 as shown by arrows 1102, and displaces the drug from drug reservoir 906 through outlet 1104. Consequently, the delivery rate is solely dependent on the osmotic properties of the osmotic agent such as salt and not on the drug itself. Therefore, any liquid drug may be delivered by cartridge 804 at the same delivery rate.

A constant delivery rate of a two-chamber/compartment cartridge 804 that acts as an osmotic pump over the whole delivery duration, 'D', is derived by its state before insertion (FIG. 11A) and the state at the end of lifetime of the cartridge 804 (FIG. 11B). The storage capacity (volume of drug reservoir 906, '$V_d$') must be almost as large as described in Eq. 4 to deliver with the rate '$\Phi$' for the period 'D'.

$$V_d = (D \cdot \Phi)/0.95 \quad [\text{Eq. 4}]$$

The volume '$V_o$' of the osmotic reservoir 904 and mass '$M_o$' of the osmotic agent are dependent on density of the osmotic agent (Eq. 5). Zero-order release may be achieved if at the end of lifetime (FIG. 11B), the solution within the enlarged ($V_o + V_d$) osmotic reservoir 904 is still a saturated solution S (Eq. 6). The adequate proportion of both chambers/compartments may be determined by Eq. 7.

$$M_o = \rho_o \cdot V_o \quad [\text{Eq. 5}]$$

$$M_o = S \cdot (V_o + V_d) \quad [\text{Eq. 6}]$$

$$V_o/V_d = S/(\rho_o - S) \quad [\text{Eq. 7}]$$

From fabrication point of view, if flexible barrier membrane 908 is removed from the two-chamber design, then a single chamber design is generated.

With reference to FIGS. 12A and 12B, a front view and a back view respectively of cartridge 804, are illustrated, in accordance with an embodiment of the invention. As shown in FIG. 12A, cartridge 804 includes outlets 1104a and 1104b. Although only two outlets are shown, a person skilled in the art will appreciate that a single or more than two outlets may be designed for cartridge 804. Further, in this view, semi-permeable/osmotic membrane 902 is also visible.

As shown in FIG. 12b, cartridge 804 includes magnets 1204a and 1204b disposed on the housing. Magnets 1204a and 1204b are used to insert/remove cartridge from receptacle 802 and base station 806. Magnets 1204a and 1204b may be Neodymium Iron Boron (NdFeB) square magnets having a typical dimension of 1.6 mm×1.0 mm×0.5 mm. Further, as shown, magnets 1204a and 1204b are located on top of cartridge 804 that are used to mount cartridge 804 within the receptacle 802 of the partial removable prosthesis. A person skilled in the art will appreciate that the dimensions of the magnets mentioned are exemplary and therefore, other dimensions suitable to the application may be used. Magnets 1204a and 1204b are embedded in the walls of the barrier polymers, and may be encapsulated by Parylene C to prevent the corrosion. Further, other materials that are less or not prone to corrosion may be selected, for example, Samarium Cobalt (SmCo).

Further, every cartridge 804 may have its own identification system. Therefore, cartridge 804 includes a Radio-Frequency Identification (RFID) tag 1202 and a micro-coil with dimensions in the range of 1 mm×1.6 mm to 2 mm×1.6 mm. In an embodiment of the invention, cartridge 804 may include bar codes that provide specific identification of cartridge 804.

With reference to FIG. 13 an exploded view of cartridge 804 is illustrated, in accordance with an embodiment of the invention. As shown, cartridge 804 includes semi-permeable membrane 902, osmotic reservoir 904, flexible barrier membrane 908, drug reservoir 906, magnets 1204a and 1204b, and RFID tag 1202, and a magnet fixing system 1302.

As shown, the housing of cartridge 804 is formed by drug reservoir 906 and osmotic reservoir 904. In an embodiment of the invention, the material of drug reservoir 906 and osmotic reservoir 904 may be bio-compatible cyclic olefin copolymer COC 8007S04 (TOPAS Advanced Polymers GmbH, Frankfurt-Höchst, Germany). COC is generally preferred due its stiffness, barrier properties against water, biocompatibility and transparency (for optical fill-level). Further, COC is also used in common tablet blister packaging. However, a person skilled in the art will appreciate that any other bio-compatible material can be selected. Also, both drug reservoir 906 and osmotic reservoir 904 may be produced by micro-injection molding. The design of cartridge 804 is free of burrs to prevent violations of the buccal mucosa.

As discussed above, cartridge 804 is actuated due to osmotic pumping principle. For regulatory aspects, materials that are commonly used for pharmaceutical drug delivery devices or medical devices (e.g. FDA-approved) are used. Osmotic coatings of Cellulose Acetate or Polyamide based thin film composites (preferred because of excellent bonding properties to COC, higher pH stability) may be used as membrane material for semi-permeable membrane 902. The permeability of semi-permeable membrane 902 together with the osmotic pressure of the osmotic agent filled in osmotic reservoir 904, defines the delivery rate of drug from cartridge 804. The delivery rate in turn determines the duration for which the cartridge 804 may be used (at constant delivery rate).

Flexible barrier membrane 908 includes a material that has excellent barrier properties against water transmission, for example polymers like Ethylene vinyl acetate (EVA), styrene block copolymers based on isoprene, ethylene, propylene or butadiene (SEBS), (SBS), (SEPS), (SIS) or fluoropolymers such as PolyVinylidene Chloride (PVdC) that are also used in pharmaceutical packaging. Flexible barrier membrane 908 may only be used if the drug is stored as a solution.

FIGS. 14A and 14B illustrate the outer surface of the cartridge 804. The FIG. 14A shows an outlet capillary of cartridge 804, in accordance with an embodiment of the invention. The support structures X1 of the drug reservoir serve to protect the flexible barrier membrane 908 during actuation. The drug in the drug reservoir 906 is expelled out from the cartridge 804 through an outlet 1104. Further, a magnified view of the outlet 1104 is shown in the FIG. 14B, in accordance with an embodiment of the invention. Further, the structure for re-directing the flow is depicted in conjunction with FIG. 16B.

FIG. 15A illustrates a magnified view of osmotic reservoir 904 from outside cartridge 804 (that directly interfaces with the external environment, such as saliva), in accordance with an embodiment of the invention. FIG. 15B illustrates a magnified view of osmotic reservoir 904 from inside the cartridge 804 (that directly interfaces with the osmotic agent), in accordance with an embodiment of the invention. The outer regions and the entire surface of osmotic reservoir 904 have an eroded appearance. Water from saliva enters the osmotic reservoir 904 from an inlet wall 1502. The inlet wall 1502 has four slots, through which the saliva enters into the osmotic reservoir 904. In an embodiment of the invention, each of the slot having a surface area in the range of 2 mm$^2$ to 2.5 mm$^2$ and most preferably 2.35 mm$^2$, compose a total orifice area in the range of 8 mm$^2$ to 10 mm$^2$, and preferably 9.40 mm$^2$ on semi-permeable membrane 902. However, a person skilled in the art will appreciate that other dimensions or area can be selected based on the application.

FIG. 16A illustrates a magnified view of drug reservoir 906 from outside cartridge 804 (that directly interfaces with the external environment, such as the receptacle 802), in accordance with an embodiment of the invention. FIG. 16B illustrates a magnified view of drug reservoir 906 from inside cartridge 804 (that directly interfaces with the drug), in accordance with an embodiment of the invention. The surface of drug reservoir 906 is completely polished from the outside and inside the middle part to ensure better readability of the fill-level.

FIG. 17 illustrates the stages in preparation of receptacle 802 as part of a partial removable prosthesis, in accordance with an embodiment of the invention. In an embodiment of the invention, a model of two mandibular molar teeth may be used to produce a two-part PolyDiMethylSiloxane (PDMS) µm high quality stereo lithographic casting model 1702 that may later on also be extracted from patient's individual CAD/CAM data. From each part a PolyDiMethylSiloxane (PDMS) negative model 1704 is molded by using, for example, duplication silicone. Further, a methylmethacrylate based dental prosthetic acryl may be used to produce replicas of the original tooth model with integrated receptacle 1706, in accordance with an embodiment. Therefore, mega CRYL N (as available from Schwarzmann GmbH, Regensburg, Germany) may be mixed in the ratio of 2:1 by weight of polymer (powder) and monomer (liquid) and poured into the PDMS casting model. Curing may be done, for example, within 15 min in a recipient by 40° C. and 1 bar pressure overload, to circumvent trapped air bubbles. Further, a part for the magnetic attachment is incorporated within integrated receptacle 1706.

Typically, the components of the partial removable prosthesis have to be functional for years and thus special emphasis may be taken for its material selection. An acrylic crown customizes an integrated receptacle 1706 into an oral cavity for irritation, haptic and cosmetic aspects. Therefore, a dental prosthetic acryl may be used that is biocompatible, conform to standards such as ISO 20795-1/Type 2/Class 1 and also used in common dentures.

FIG. 18 illustrates an integrated receptacle 1706 with a partial model of a cartridge, such as the cartridge 804, in accordance with an embodiment of the invention. This FIG. 18 illustrates exemplary relative dimensions of integrated receptacle 1706 and cartridge 804.

FIGS. 19A and 19B illustrate various stages of using an assistive tool, in accordance with an embodiment of the invention. Assistive tool 808 enables the patient to insert and remove cartridge 804 into and from receptacle 802, and for insertion or removal thereof into or from base station 806. Further, base station 806 may include a fill-level measurement system for detecting the level of drug/medication in cartridge 804.

Assistive tool 808 may include one or more magnets to insert/remove cartridge 804. Further, there are also various alternatives to realize the magnetic attachment system. For example, the magnets may be present on both receptacle 802 and cartridge 804. Further, it could also be thought that there is only a magnet on cartridge 804 or only a magnet on receptacle 802. Therefore, assistive tool 808 may include a metal surface that may be attached to cartridge 804 due to magnetic forces. Moreover, it could also be thought that the magnets and the magnetizable steel on cartridge 804 are combined in one design.

The magnetic attachment principle may be most useable for various patients. Generally, multiple sub-principles may be enumerated for such a magnetic attachment system, for example:

1. Overruling magnetic forces:
    weakest forces during insertion: magnetic force between insertion side of assistive tool 808 and a buccal side of the cartridge 804.
    medium forces during wearing cartridge 804 in receptacle 802. The forces are strong enough that cartridge 804 is not lost during wearing.

strongest forces during removal of cartridge 804: magnetic force between removal side of assistive tool 808 and buccal side of cartridge 804.

2. Electromagnetic switchable permanent holding magnet
3. Mechanical ON/OFF switch of a magnet Typical stages of using assistive tool 808 are shown with reference to FIGS. 19A and 19B. As shown in FIG. 19A, at stage 1902, assistive tool 808 may be inserted or removed from a docking section on base station 806. In stage 1904, assistive tool 808 is shown to select cartridge 804 from a tray 1912. Further, stage 1906 illustrates checking of fill level (shown in inset 1914) of cartridge 804 at base station 806. In FIG. 19B, at stage 1908, assistive tool 808 is shown to remove cartridge 804 from base station 806, and at stage 1910, cartridge 804 is inserted/removed from receptacle on a jaw 912 with the help of assistive tool 808.

With reference to FIG. 20, base station 806 is illustrated, in accordance with an embodiment of the invention. As shown, base station 806 may include a docking section 2002 for docking assistive tool 808 at base station 806. Moreover, base station 806 may include drug-level indicators 2006 to indicate the level of drug in cartridge 804. For example, drug-level indicators 2006 may include light emitting diodes, a liquid crystal display, an audio indicator, and/or a combination of these. Base station 806 may be powered with batteries or an external power may be provided such as Alternating Current (AC) or Direct Current (DC).

Further, base station 806 includes a cartridge-docking section 2004 for docking cartridge 804. Cartridge 804 may be identified before and after usage and the administered amount of drug may be measured by using base station 806. The cartridge identification may be based on systems such as Radio Frequency Identification (RFID) or bar codes. A generally know product, is the Mic3® that offers a memory capacity from 64 bit read only up to 32 kbit read write, and is the smallest RFID transponder worldwide with integrated coil on the chip. With a size of 2.1×2.0×0.5 mm, these transponders are suitable for the identification of least objects. Mic3® transponders are also suitable for short-term mass production and have a wide temperature range as well as a high reliability. In an embodiment of the invention, such an RFID tag may be used for cartridge 804, for example, an RFID tag with 64 bit read only and a size of 1.6×1.0×0.5. However, a person skilled in the art will appreciate that other type of tag with different characteristics may also be used based on the requirement of the system.

Base station 806 may communicate with a supervising center, for example a telemedical service center. In an embodiment of the invention, base station 806 may transmit information acquired from cartridge 804, such as identification of cartridge 804, fill level, and/or other characteristics of cartridge 804 and/or the drug. Base station 806 may communicate by using various protocols such as Zigbee, Bluetooth, Infrared with a mobile gateway 2008 that may in turn forward the acquired information to a remote monitoring and supervising center. In an embodiment of the invention, base station 806 may be capable of using mobile/wifi communication. Therefore, base station 806 may use protocol standards such as 2G/3G/4G or wireless to communicate with mobile gateway 2008 or directly to the remote monitoring and supervising center.

Base station 806 may use Light Emitting Diodes (LEDs) to measure the fill level of drug in a cartridge. The particular challenge to the fill level measurement principle is that there is no liquid or gas detection, but a liquid or liquid detection. The fill level measurement is further explained in conjunction with FIG. 21.

FIG. 21 illustrates fill level measurement method of cartridge, such as the cartridge 804, in accordance with an embodiment of the invention. In an embodiment of the invention, base station 806 includes one or more Light Emitting Diodes (LEDs) and a receiving photodiode situated opposite to the LEDs for identifying the level of drug in cartridge 804. The principle is based on two light beams, measured through cartridge 804 at one or more opposite photodiodes. In case of a single chamber cartridge 804, one LED 2102 and one receiving photodiode 2104 are used. Initially, when the drug chamber 906 is filled with solid drug, the drug blocks the light beam from the LED 2102 to reach the receiving photodiode 2104. As a result, no light is received by the receiving photodiode 2104. Further, when the drug becomes dissolved due to usage, the light beam may penetrate cartridge 804 and is received by the receiving photodiode 2104.

In case of a two-chamber cartridge 804, two LEDs and one receiving photodiode are used. The osmotic reservoir 904 includes salt and a dye. The dye gets dissolved in water that enters the osmotic reservoir 904 and forms dyed salt solution. Initially before the usage, the LEDs are so situated around the cartridge 804 that the light beams of both LEDs may penetrate cartridge 804 and are received by the receiving photodiode. After/during usage, the flexible barrier membrane 908 of cartridge 804 is deflected and comes in the path of the light beam of one of the LEDs. As a result, one LED beam is blocked by the membrane 908. Further, this light beam is more and more absorbed by the dyed solution underneath the semi permeable membrane 902 (dye included in osmotic reservoir 904 which does NOT contain drug). The second LED beam penetrates both the membranes (semi-permeable and barrier) or dye and is always received by the photodiode. The second light beam may serve as a reference to compensate environmental parameters such as, but not limited to, ambient light, contaminated or scratched slot, and so forth. Therefore, the fill level may be estimated. Moreover, the wavelength of the light beams may be different.

In another embodiment of the invention, the lights of different wavelengths are chosen in a way that the light from the first LED is in the absorptive maximum of a dye in the osmotic reservoir 904 while the second light beam from the second LED may penetrate cartridge 804 without loss. The wavelengths are chosen in a way such that a first light beam may penetrate cartridge 804 without absorption when cartridge 804 is empty of liquid drug and hence the dye is not suspended or diluted in cartridge 804. The other light beams are absorbed at different absorption levels depending upon the concentration of the dye in the liquid drug. As a result, the amount of drug remaining in cartridge 804 may be estimated. Exemplary stages during usage of a two-chamber cartridge are explained in conjunction with FIG. 22.

Further, this system/principle is insusceptible to saliva on cartridge 804 or to changes of ambient conditions (i.e. ambient light). Besides a coloring of the osmotic reservoir, it could also be envisaged to use additives in the flexible membrane, i.e. UV absorbing additives, causing the measurement principle to be quantitatively transferred to other wavelengths or concentrations. In an embodiment of the invention, the osmotic reservoir 904 is colored with the dye Allura Red AC (E129). According to European Directive 94/63/EC, the dye is safe and harmless. Further, according to (German) drug regulations the (AMFarbV), the dye may be also used as additive in drugs. Therefore, the patient may measure drug level and change a cartridge preloaded with the drug on a daily basis.

FIG. 22 illustrates exemplary stages during use of a two-chamber cartridge, in accordance with an embodiment of the invention. Stages 2204*a*, 2204*b*, 2204*c*, 2204*d*, and 2204*e* are various stages during the use of the two-chamber cartridge. Stage 2204*a* is the initial stage where the flexible membrane 908 is not yet deflected and therefore, first light beam 2200 and second light beam 2202 may penetrate through the cartridge and detected at a receiving photodiode. Thereafter, during the usage, the flexible membrane 908 of the cartridge 804 is deflected due to osmotic pressure. Therefore, the osmotic chamber 904 containing the dye gradually expands into the drug-filled chamber 906. As a result, first light beam 2200 is more and more absorbed by the dye contained in the osmotic chamber 904, while second light beam 2202 may still penetrate through the cartridge 804. Finally, at stage 2204*e*, first light beam 2200 is completely absorbed by the dye and second light beam 2202 may still penetrate the cartridge and be detected at the receiving photodiode.

FIG. 23A illustrates transmittance spectrum of Allura Red AC. As shown, transmittance of Allura Red AC varies with the wavelength of light beam used. Allura Red AC is a type of dye that may be used in the cartridge to determine fill level of drug present therein. Further, the fill level, of the drug in accordance with an embodiment of the invention, may be determined by detecting the amount of the light beam that is allowed to be transmitted through the Allura Red AC. As shown, at the wavelength 500 nm, transmittance of Allura Red AC is lower as compared to transmittance at the wavelength of 600 nm. Therefore, more of the light is absorbed by Allura Red AC when the wavelength is 500 nm as compared to absorption of light at the wavelength of 600 nm. A person skilled in the art will appreciate that any other dye with similar properties may be used.

FIG. 23B illustrates theoretical sensor signal of a used and an unused cartridge. A curve 2302 illustrates variation in sensor signal before usage of cartridge 804 with wavelength of the light beam. Similarly, a curve 2304 illustrates variation in sensor signals after usage of cartridge 804 with wavelength of the light beam.

FIG. 24A illustrates motor fluctuations in a standard Parkinson therapy. Conventionally, advanced stages of disorders such as Parkinson's disease require invasive administration of drugs into the bloodstream, e.g. by subcutaneous pumps or duodenal catheters. Specifically, FIG. 24A shows fluctuating clinical effects in the standard Parkinson's disease. Further, the clinical effect may be controlled by utilizing the system and method corresponding to the present invention, as explained further in conjunction with FIG. 24B.

FIG. 24B illustrate motor fluctuations in aimed drug profile with the system and method of the present invention. As shown, the present invention is aimed to be a far less invasive intraoral system for the self-medicated treatment of Parkinson's disease. Specifically, FIG. 24B shows controlled clinical effect due to a constant release of drug to the buccal mucosa and consequently into the bloodstream, thereby avoiding first-pass metabolism or acts as a continuous enteral infusion pump (e.g. for Levodopa).

Advantageously, the disclosed system provides a controlled rate of drug release utilizing a less comprehensive therapy plan. The system employs an osmotic principle in a cartridge that helps in releasing a controlled amount of drug, hence avoiding over dosage or less dosage of the drug intake. Additionally, owing to this system, the clinical effect is not fluctuating since the patient may not be required to take the medicine/drug at defined time intervals. Furthermore, the system works for longer periods of time, useful for chronic diseases. Additionally, the system avoids first-pass metabolism and acts as a continuous enteral infusion pump. Moreover, the system comprises a removable cartridge and a base station, where the base station provides for the communication between the cartridge and a telemedical service. This may help in diagnosing any abnormalities in the drug or in cartridge. Further, the system is simple and easy to use by any age-group of people.

Having discussed the exemplary embodiments the system and device for controlled release of drug, it should be appreciated that a method of providing controlled release of drug is also contemplated. A system or device for controlled drug release is provided. The system comprises a removable drug-containing cartridge that is actuated by an osmotic pumping principle, a receptacle to hold the cartridge in the oral cavity and a base station for: identification of the cartridge, determination of cartridge fill level, and communication with a telemedical service. The system also comprises an assistive tool to help the user in the insertion and removal of said cartridge into and from said receptacle and into and from said base station. The receptacle being adapted for insertion to an oral cavity of a subject.

As one of ordinary skill in the art will appreciate, the example system and method described herein may be modified. For example, certain steps may be omitted, certain steps may be carried out concurrently, and other steps may be added. Although particular embodiments of the invention have been described in detail, it is understood that the invention is not limited correspondingly in scope, but includes all changes, modifications and equivalents coming within the spirit and terms of the claims appended hereto.

While the invention has been described in connection with what is presently considered to be the most practical and various embodiments, it is to be understood that the invention is not to be limited to the disclosed embodiments, but on the contrary, is intended to cover various modifications and equivalent arrangements included within the spirit and scope of the appended claims.

This written description uses examples to disclose the invention, including the best mode, and also to enable any person skilled in the art to practice the invention, including making and using any devices or systems and performing any incorporated methods. The patentable scope the invention is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for controlled oral drug delivery, comprising:
   a removable device comprising a drug to be delivered, wherein the drug is delivered based on osmotic pressure generated in the removable device;
   a receptacle to hold the removable device in an oral cavity; and
   a base station configured to dock the removable device for determining information about one or more characteristics of the removable device, wherein the base station further comprises:
   a plurality of light sources configured to emit one or more light beams; and
   a plurality of receiving photodiodes situated opposite to the plurality of light sources, and configured to receive the one or more light beams, wherein a deflection of a flexible barrier membrane absorbs at least one of the one or more light beams enabling detection of a fill level of a drug chamber.

2. The system of claim 1, wherein the removable device comprises:
a housing for removable insertion into the oral cavity, the housing comprising:
a drug chamber comprising the drug to be delivered; and
an osmotic membrane enclosing the drug chamber and generating the osmotic pressure, wherein the osmotic pressure membrane interfaces with saliva.

3. The system of claim 1, wherein the removable device comprises:
a housing for removable insertion into the oral cavity, the housing comprising:
a drug chamber comprising the drug to be delivered; and
an osmotic chamber comprising the osmotic agent enclosed by a flexible barrier membrane on a first end and an osmotic membrane at a second end, wherein the flexible barrier membrane separates the osmotic chamber from the drug chamber and the osmotic membrane interfaces with saliva,
and wherein the flexible barrier membrane is actuated by osmotic pressure in the osmotic chamber to deliver the drug from the drug chamber.

4. The system of claim 2 or 3, wherein the drug chamber further comprising an outlet for delivering the drug.

5. The system of claim 2 or 3, wherein the removable device comprises one or more magnets disposed on the housing for removable insertion and retention from the receptacle.

6. The system of claim 2 or 3, wherein the removable device further comprises an identification tag disposed on the housing.

7. The system of claim 3, wherein the osmotic agent comprises a hygroscopic material selected from a group comprising essentially of solid salt, saccharides, hydrogels, and polymers.

8. The system of claim 3, wherein the osmotic chamber further comprises a dye capable of being diluted with water being part of the saliva and flowing through the osmotic membrane into the osmotic chamber.

9. The system of claim 1, wherein the base station further comprises:
at least one light source; and
a receiving photodiode situated opposite to the at least one light source,
wherein the at least one light source is configured to emit one or more light beams of different wavelengths, wherein the wavelengths being based on one or more light absorption characteristics of the drug or an additional dye to detect a fill level of the drug chamber.

10. The system of claim 1, wherein the receptacle is attached to the oral cavity by using a dental appliance, wherein the dental appliance is selected from a group comprising essentially of a removable denture, a prosthetic tooth crown, a dental bridge, a moral band, a bracket, a mouth guard, a night guard, and a dental implant.

11. The system of claim 1, wherein the one or more characteristics of the removable device comprises at least one of an identification tag and a fill level of the removable device.

12. The system of claim 1, wherein the base station further comprises an assistive tool configured to enable insertion and removal of the removable device into and from the receptacle.

13. The system of claim 1, wherein the base station is further configured to communicate the information to an external telemedical device.

14. A system for controlled oral drug delivery, comprising:
a removable device comprising a drug to be delivered, wherein the drug is delivered based on osmotic pressure generated in the removable device;
a receptacle to hold the removable device in an oral cavity;
a base station configured to dock the removable device for determining information about one or more characteristics of the removable device, wherein the base station further comprises:
a plurality of light sources configured to emit one or more light beams; and
a plurality of receiving photodiodes situated opposite to the plurality of light sources and configured to receive the one or more light beams, wherein a deflection of a flexible barrier membrane absorbs at least one of the one or more light beams enabling detection of a fill level of the drug chamber; and
an assistive tool configured to enable insertion and removal of the removable device into and from the receptacle.

15. The system of claim 14, wherein the removable device comprises:
a housing for removable insertion into the oral cavity, the housing comprising:
a drug chamber comprising the drug to be delivered; and
an osmotic membrane enclosing the drug chamber and generating the osmotic pressure, wherein the osmotic membrane interfaces with saliva.

16. The system of claim 14, wherein the removable device comprises:
a housing for removable insertion into the oral cavity, the housing comprising:
a drug chamber comprising the drug to be delivered; and
an osmotic chamber comprising the osmotic agent enclosed by a flexible barrier membrane on a first end and an osmotic membrane at a second end, wherein the flexible barrier membrane separates the osmotic chamber from the drug chamber and the osmotic membrane interfaces with saliva,
and wherein the flexible barrier membrane is actuated by osmotic pressure in the osmotic chamber to deliver the drug from the drug chamber.

17. The system of claim 14, wherein the osmotic pressure is generated by inflow of water from saliva to enter the osmotic chamber due to concentration gradient created across the osmotic membrane.

* * * * *